United States Patent
Kim et al.

(10) Patent No.: US 7,399,272 B2
(45) Date of Patent: Jul. 15, 2008

(54) METHODS AND APPARATUS PROVIDING SUCTION-ASSISTED TISSUE ENGAGEMENT

(75) Inventors: David J. S. Kim, Maple Grove, MN (US); Eric J. Boone, St. Michael, MN (US)

(73) Assignee: Medtronic, Inc., Minneapolis, MN (US)

( * ) Notice: Subject to any disclaimer, the term of this patent is extended or adjusted under 35 U.S.C. 154(b) by 386 days.

(21) Appl. No.: 10/807,888

(22) Filed: Mar. 24, 2004

(65) Prior Publication Data

US 2005/0215851 A1    Sep. 29, 2005

(51) Int. Cl.
*A61F 13/00* (2006.01)
*A61B 1/32* (2006.01)

(52) U.S. Cl. .................... 600/37; 600/201; 600/210; 600/229

(58) Field of Classification Search ......... 128/897–899; 604/164, 264, 272, 280; 600/16, 36–37, 600/103, 114, 121, 125, 127, 129, 153, 160, 600/201, 204, 205, 210, 213, 216–219, 227–235; 606/2, 7, 13–16, 32, 41, 129, 139, 167, 185, 606/191, 232–234
See application file for complete search history.

(56) References Cited

U.S. PATENT DOCUMENTS

| | | | |
|---|---|---|---|
| 452,131 A | 5/1891 | Haughawout | |
| 2,590,527 A | 3/1952 | Fluck | 123/67 |
| 3,577,982 A | 5/1971 | La Par | 128/2 R |
| 3,720,433 A | 3/1973 | Rosfelder | 294/64 R |
| 3,783,873 A | 1/1974 | Jacobs | 128/303 R |
| 3,786,815 A | 1/1974 | Ericson | 128/321 |
| 3,858,926 A | 1/1975 | Ottenhues | 294/64 R |
| 3,916,909 A | 11/1975 | Kletschka et al. | 128/54 |
| 3,951,138 A | 4/1976 | Akopov | 128/17 |
| 3,983,863 A | 10/1976 | Janke et al. | 128/1 R |
| 3,999,795 A | 12/1976 | Barker | 294/64 R |
| 4,047,532 A | 9/1977 | Phillips et al. | 128/303 R |
| 4,049,000 A | 9/1977 | Williams | 128/276 |
| 4,049,002 A | 9/1977 | Kletschka et al. | 128/318 |
| 4,096,864 A | 6/1978 | Kletschka et al. | 128/354 |
| 4,306,561 A | 12/1981 | De Medinaceli | 128/303.13 |
| 4,314,568 A | 2/1982 | Loving | 128/327 |
| 4,350,160 A | 9/1982 | Kolesov et al. | 128/334 |
| 4,366,819 A | 1/1983 | Kaster | 128/334 C |
| 4,368,736 A | 1/1983 | Kaster | 128/334 C |

(Continued)

FOREIGN PATENT DOCUMENTS

DE    G 9004513.0    4/1990

(Continued)

OTHER PUBLICATIONS

Mammary Artery-Coronary Artery Anastomosis as Method of Treatment for Angina Pectoris, V.I Kolessov, MD/Thoracic and Cardiovascular Surgery, vol. 54, No. 4, Oct. 1967 pp. 535-544.

(Continued)

*Primary Examiner*—John P Lacyk
(74) *Attorney, Agent, or Firm*—Mike Jaro; Jeffrey J. Hohenshell

(57) ABSTRACT

A device for providing suction to tissue is disclosed. A method of suctioning tissue is also disclosed.

36 Claims, 7 Drawing Sheets

U.S. PATENT DOCUMENTS

| | | | | |
|---|---|---|---|---|
| 4,428,368 | A | 1/1984 | Torii | 128/38 |
| 4,447,227 | A | 5/1984 | Kotsanis | 604/95 |
| 4,463,980 | A | 8/1984 | Orii | 294/64 R |
| 4,627,421 | A | 12/1986 | Symbas et al. | 128/20 |
| 4,637,377 | A | 1/1987 | Loop | 128/1 R |
| 4,646,747 | A | 3/1987 | Lundbäck | 128/643 |
| 4,688,570 | A | 8/1987 | Kramer et al. | 128/305 |
| 4,711,247 | A | 12/1987 | Fishman | 128/743 |
| 4,718,418 | A | 1/1988 | L'Esperance, Jr. | 128/303.1 |
| 4,726,356 | A | 2/1988 | Santilli et al. | 128/20 |
| 4,736,749 | A | 4/1988 | Lundback | 128/643 |
| 4,767,142 | A | 8/1988 | Takahashi et al. | 294/64.1 |
| 4,808,163 | A | 2/1989 | Laub | 604/105 |
| 4,852,552 | A | 8/1989 | Chaux | 128/20 |
| 4,854,318 | A | 8/1989 | Solem et al. | 128/346 |
| 4,865,019 | A | 9/1989 | Phillips | 128/20 |
| 4,892,343 | A | 1/1990 | Hall | 294/64.1 |
| 4,904,012 | A | 2/1990 | Nishiguchi et al. | 294/64 |
| 4,925,443 | A | 5/1990 | Heilman et al. | 600/16 |
| 4,955,896 | A | 9/1990 | Freeman | 606/210 |
| 4,962,758 | A | 10/1990 | Lasner et al. | 128/41 |
| 4,973,300 | A | 11/1990 | Wright | 600/37 |
| 4,989,587 | A | 2/1991 | Farley | 128/20 |
| 4,991,578 | A | 2/1991 | Cohen | 128/419 D |
| 5,009,660 | A | 4/1991 | Clapham | 606/166 |
| 5,011,469 | A | 4/1991 | Buckberg et al. | 604/4 |
| 5,053,041 | A | 10/1991 | Ansari et al. | 606/148 |
| 5,098,369 | A | 3/1992 | Heilman et al. | 600/16 |
| 5,108,412 | A | 4/1992 | Krumeich et al. | 606/166 |
| 5,119,804 | A | 6/1992 | Anstadt | 128/64 |
| 5,131,905 | A | 7/1992 | Grooters | 600/16 |
| 5,133,737 | A | 7/1992 | Grismer | 606/205 |
| 5,167,223 | A | 12/1992 | Koros et al. | 128/20 |
| 5,171,254 | A | 12/1992 | Sher | 606/166 |
| 5,207,467 | A | 5/1993 | Smith | 294/64.1 |
| 5,287,861 | A | 2/1994 | Wilk | 128/898 |
| 5,290,082 | A | 3/1994 | Palmer et al. | 294/64.1 |
| 5,300,087 | A | 4/1994 | Knoepfler | 606/207 |
| 5,324,087 | A | 6/1994 | Shimose et al. | 294/64.1 |
| 5,336,252 | A | 8/1994 | Cohen | 607/119 |
| 5,365,921 | A | 11/1994 | Bookwalter et al. | 128/20 |
| 5,372,124 | A | 12/1994 | Takayama et al. | 128/4 |
| 5,374,277 | A | 12/1994 | Hassler | 606/207 |
| 5,383,840 | A | 1/1995 | Heilman et al. | 600/17 |
| 5,417,709 | A | 5/1995 | Slater | 606/205 |
| 5,425,705 | A | 6/1995 | Evard et al. | 604/28 |
| 5,437,651 | A | 8/1995 | Todd et al. | 604/313 |
| 5,452,733 | A | 9/1995 | Sterman et al. | 128/898 |
| 5,472,438 | A | 12/1995 | Schmit et al. | 606/1 |
| 5,503,617 | A | 4/1996 | Jako | 600/201 |
| 5,509,890 | A | 4/1996 | Kazama | 600/37 |
| 5,545,123 | A | 8/1996 | Ortiz et al. | 600/235 |
| 5,556,147 | A | 9/1996 | Somekh et al. | 294/64.1 |
| 5,607,421 | A | 3/1997 | Jeevanandam et al. | 606/15 |
| 5,613,937 | A | 3/1997 | Garrison et al. | 600/201 |
| 5,667,624 | A | 9/1997 | Akimoto et al. | 156/389 |
| 5,702,420 | A | 12/1997 | Sterling et al. | 606/205 |
| 5,727,569 | A | 3/1998 | Benetti et al. | 128/898 |
| 5,730,757 | A | 3/1998 | Benetti et al. | 606/198 |
| 5,749,892 | A | 5/1998 | Vierra et al. | 600/204 |
| 5,772,583 | A | 6/1998 | Wright et al. | 600/232 |
| 5,782,746 | A | 7/1998 | Wright | 600/37 |
| 5,799,661 | A | 9/1998 | Boyd et al. | 128/898 |
| 5,807,243 | A | 9/1998 | Vierra et al. | 600/204 |
| 5,827,216 | A | 10/1998 | Igo et al. | 604/21 |
| 5,836,311 | A | 11/1998 | Borst et al. | 128/897 |
| 5,865,730 | A | 2/1999 | Fox et al. | |
| 5,875,782 | A | 3/1999 | Ferrari et al. | 128/898 |
| 5,888,247 | A | 3/1999 | Benetti | 623/66 |
| 5,894,843 | A | 4/1999 | Benetti et al. | 128/898 |
| 5,906,607 | A | 5/1999 | Taylor et al. | 606/1 |
| 5,921,979 | A | 7/1999 | Kovac et al. | 606/1 |
| 5,927,284 | A | 7/1999 | Borst et al. | 128/898 |
| 5,947,896 | A | 9/1999 | Sherts et al. | 600/229 |
| 5,976,080 | A | 11/1999 | Farascioni | 600/213 |
| 5,976,171 | A | 11/1999 | Taylor | 606/198 |
| 6,015,378 | A | 1/2000 | Borst et al. | 600/37 |
| 6,017,304 | A | 1/2000 | Vierra et al. | 600/204 |
| 6,019,722 | A * | 2/2000 | Spence et al. | 600/210 |
| 6,032,672 | A | 3/2000 | Taylor | 128/898 |
| 6,036,641 | A | 3/2000 | Taylor et al. | 600/231 |
| 6,050,266 | A | 4/2000 | Benetti et al. | 128/898 |
| 6,063,021 | A | 5/2000 | Hossain et al. | 600/37 |
| 6,071,235 | A | 6/2000 | Furnish et al. | 600/235 |
| 6,071,295 | A | 6/2000 | Takahashi | 606/191 |
| 6,074,375 | A | 6/2000 | Stiles | 604/268 |
| 6,110,187 | A | 8/2000 | Donlon | 606/151 |
| 6,120,436 | A | 9/2000 | Anderson et al. | 600/201 |
| 6,132,370 | A | 10/2000 | Furnish et al. | 600/235 |
| 6,139,492 | A | 10/2000 | Vierra et al. | 600/204 |
| 6,149,583 | A | 11/2000 | Vierra et al. | 600/204 |
| 6,152,874 | A | 11/2000 | Looney et al. | 600/214 |
| 6,161,543 | A | 12/2000 | Cox et al. | |
| 6,183,486 | B1 | 2/2001 | Snow et al. | 606/151 |
| 6,206,827 | B1 | 3/2001 | Chin et al. | 600/217 |
| 6,210,323 | B1 | 4/2001 | Gilhuly et al. | 600/210 |
| 6,213,941 | B1 | 4/2001 | Benetti et al. | 600/235 |
| 6,254,535 | B1 | 7/2001 | Furnish et al. | 600/213 |
| 6,290,644 | B1 | 9/2001 | Green, II et al. | 600/235 |
| 6,306,085 | B1 | 10/2001 | Farascioni | 600/213 |
| 6,315,717 | B1 | 11/2001 | Benetti et al. | 600/210 |
| 6,328,688 | B1 | 12/2001 | Borst et al. | 600/37 |
| 6,331,158 | B1 | 12/2001 | Hu et al. | 600/232 |
| 6,334,843 | B1 | 1/2002 | Borst et al. | 600/37 |
| 6,338,712 | B2 * | 1/2002 | Spence et al. | 600/201 |
| 6,346,077 | B1 | 2/2002 | Taylor et al. | 600/204 |
| 6,350,229 | B1 | 2/2002 | Borst et al. | 600/37 |
| 6,364,826 | B1 | 4/2002 | Borst et al. | 600/37 |
| 6,371,906 | B1 | 4/2002 | Borst et al. | 600/37 |
| 6,379,297 | B1 | 4/2002 | Furnish et al. | 600/213 |
| 6,394,948 | B1 | 5/2002 | Borst et al. | 600/37 |
| 6,394,951 | B1 | 5/2002 | Taylor et al. | 600/210 |
| 6,464,629 | B1 | 10/2002 | Boone et al. | 600/37 |
| 6,464,630 | B1 | 10/2002 | Borst et al. | 600/37 |
| 6,471,644 | B1 | 10/2002 | Sidor, Jr. | 600/204 |
| 6,558,318 | B1 | 5/2003 | Daniel et al. | 600/213 |
| 6,602,183 | B1 | 8/2003 | Levi et al. | 600/37 |
| 6,610,008 | B1 * | 8/2003 | Spence et al. | 600/210 |
| 6,740,028 | B2 | 5/2004 | Borst | |
| 6,755,780 | B2 | 6/2004 | Borst et al. | |
| 6,758,808 | B2 * | 7/2004 | Paul et al. | 600/229 |
| 6,849,075 | B2 | 2/2005 | Bertolero et al. | |
| 6,905,498 | B2 | 6/2005 | Hooven | |
| 6,932,811 | B2 | 8/2005 | Hooven | |
| 2002/0013809 | A1 | 1/2002 | Hashimoto et al. | 709/203 |
| 2002/0045888 | A1 | 4/2002 | Ramans et al. | 606/1 |
| 2002/0077532 | A1 * | 6/2002 | Gannoe et al | 600/232 |
| 2002/0095067 | A1 | 7/2002 | Guenst et al. | 600/37 |
| 2002/0099268 | A1 * | 7/2002 | Paul et al. | 600/201 |
| 2003/0078470 | A1 | 4/2003 | Borst | |
| 2004/0106918 | A1 | 6/2004 | Cox et al. | |

FOREIGN PATENT DOCUMENTS

| | | |
|---|---|---|
| DE | 29708050 | 5/1997 |
| EP | 0 167 345 A1 | 1/1986 |
| EP | 0 293 760 A2 | 5/1988 |
| EP | 0 432 560 A2 | 11/1990 |
| EP | 0 630 629 A1 | 12/1994 |
| EP | 0 668 058 A1 | 8/1995 |
| EP | 0 808 606 A1 | 11/1997 |
| EP | 0 920 835 A1 | 6/1999 |
| GB | 2 140 695 A | 12/1984 |
| GB | 2 214 428 A | 9/1989 |

| | | |
|---|---|---|
| GB | 2233561 | 1/1991 |
| GB | 2 214 428 B | 6/1991 |
| GB | 2267827 | 12/1993 |
| JP | 59143408 | 8/1984 |
| JP | 01232945 | 9/1989 |
| JP | 06012045 | 1/1994 |
| JP | 02607600 | 5/1997 |
| WO | WO 87/04081 | 7/1987 |
| WO | WO 88/00481 | 1/1988 |
| WO | WO 94/03142 | 2/1994 |
| WO | WO 94/14383 | 7/1994 |
| WO | WO 94/14715 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 98/10705 | 3/1998 |
| WO | WO 98/17182 | 4/1998 |
| WO | WO 98/27869 | 7/1998 |
| WO | WO 99/16367 | 4/1999 |
| WO | 01/17437 A2 | 3/2001 |

OTHER PUBLICATIONS

Direct Myocardial Revascularization by Saphenous Vein Graft, R.G. Favaloro, MD; DG Effler, MD; LK Groves, MD; WG Sheldon, MD; and FM Sones, Jr., MD / The Annals of Thoracic Surgery, vol. 10, No. 2, Aug. 1970.

A Simple Technique and Device To Provide a Bloodless Operative Field in Coronary Artery Surgery Without Cross-Clamping the Aorta, M. Riahi, RJ Schlosser and LA Tomastis/The Journal of Thoracic and Cardiovascular Surgery, vol. 66, No. 6, Dec. 1973, pp. 974-978.

To Use or Not To Use the Pump Oxygenator in Coronary Bypass Operations, Drs. WG Trapp and R. Bisarya/The Annals of Thoracic Surgery, vol. 19, No. 1, Jan. 1975, pp. 108-109.

A Prospective Evaluation of the Pulsatile Assist Device, GL Zumbro, Jr., MD; G Shearer, CCP; ME Fishback, MD; and RF Galloway, MD / The Annals of Thoracic Surgery, vol. 28, No. 2 Aug. 1979, pp. 269-273.

Preservation of Interventricular Septal Function in Patients Having Coronary Artery Bypass Grafts Without Cardiopulmonary Bypass, CW Akins, MD; CA Boucher, MD; and GM Pohost, MD / American Heart Journal, vol. 107, No. 2, Feb. 1984, pp. 304-309.

Coronary Artery Revascularization Without Cardiopulmonary Bypass, R. Archer, DO; DA Ott, MD; R. Parravicini, MD; DA Cooley, MD; GJ Reul, MD; OH Frazier, MD; JM Duncan, MD; JJ Livesay, MD and WE Walker, MD, Texas Heart Institute Journal, vol. 11, No. 1, Mar. 1984, pp. 52-57.

Direct Myocardial Revascularization Without Cardiopulmonary Bypass, E. Buffolo; JCS Andrade, J Succi; LEV Leao; and C Gallucci. Thoac. Cardiovasc. Surgeon, 33 (1985) pp. 26-29.

Direct Coronary Surgery with Saphenous Vein Bypass Without Eigher Cardiopulmonary Bypass or Cardiac Arrest, FJ Benetti, The Journal of Cardiovascular Surgery, vol. 26, No. 3, May-Jun. 1985, pp. 217-222.

Heart-Mechanical Assist Device Interaction, JY Kresh; PLM Kerkhof; SM Goldman; and SK Brockman, Trans. Am. Soc. Artif. Intern. Organs, vol. XXXII, 1986, pp. 437-443.

Delayed Recovery of Severaly 'Stunned' Myocardium with the Support of a Left Ventricular Assist Device after Coronary Artery Bypass Graft Surgery, CM Ballantyne MD; MS verani, MD, FACC; HD Short, MD; C Hyatt, BSN, RN; GP Noon, MD, FACC, Journal of the American College of Cardiology, vol. 10, No. 3, Sep. 1987, pp. 710-712.

Long-Term Follow-up of Survivors of Postcardiotomy Circulatory Support, SA Ruzevich; KR Kanter; DG Pennington; MT Swartz; LR McBride; and DT Termuhlen, Trans. Am. Soc. Artif. Intern. Organs, vol. XXXIV, 1988, pp. 116-124.

Extended Clinical Support with an Implantable Left Ventricular Assist Device, MG McGee; SM Parnis; T Nakatani; T Myers; K Dasse; WD Hare; JM Duncan; VL Poirier; and OH Frazier, Trans Am. Soc. Artif. Intern. Organs, vol. XXXV, 1989, pp. 614-616.

Current Status of Cardiac Surgery: A 40-Year Review, WE Richenbacher, MD; JL Myers, MD, FACC; JA Walhausen, MD, FACC, Journal of American College of Cardiology, vol. 14, No. 3, Sep. 1989, pp. 535-544.

Transfemoral Placement of the Left Ventricular Assist Device "Hemopump" During Mechanical Resuscitation, KH Scholz; U Tebbe; M Chemnitius; H Kreuzer; T Schroder; JP Hering; P Uhlig; G Hellige; HJ Grone; R Autschbach; B Schorn; W Ruschewski; and H Dalichau, Thoracic and Cardiovascular Surgeon, vol. 38 (1990) pp. 69-72.

Direct Mechanical Ventricular Actuation for Cardiac Arrest in Humans, MP Anstadt, MD; RL Bartlett, MD; JP Malone, MD, FCCP; and GL Anstadt, VMD; Chest, vol. 100, No. 1, Jul. 1991.

Direct Myocardial Revascularization Without Extracorpoeal Circulation, FJ Benetti, MD; G Naselli, MD; M Wood, MD; and L Geffner, MD, Chest, vol. 100. No. 2, Aug. 1991, pp. 312-316.

Coronary Artery Bypass Without Cardiopulmonary Bypass, Pfister et al, The Annals of Thoracic Surgery, vol. 54 #6 Dec. 1992 pp. 1085-1092.

Coronary Artery Operation Supported by the Hemopump: An Experimental Study on Pig, U Lonn, MD; B Peterzen, MD; H Granfeldt, MD; and H Casimir-Ahn, MD, Ph.D. The Annals of Thoracic Surgery, vol. 58, No. 1, Jul. 1994, pp. 516-523.

Regional Cardiac Wall Immobilization for Open Chest and Closed Chest Coronary Artery Bypass Grafting on the Beating Heart: The 'Octopus' Method, Circulation, vol. 92. No. 8 Supplement 1, I-177 (Oct. 15, 1995).

A Minimally Invasive Surgical Method for Coronary Revascularization—Preliminary Experience in Five Patients, MC Robinson, DR Gross, and W Zeman, Circulation, (Oct. 15, 1995) vol. 92, No. 8, I-176.

Coronary Artery Bypass Grafting Without Cardiopulmonary Bypass and Without Interruption of Native Coronary Flow Using a Novel Astamosis Site Restraining Device ("Octopus"), C. Borst et al., Journal of the American College of Cardiology, vol. 27, No. 6, 1356-1364 (May 1996).

Cardiogenic Shock Complicating Acute Myocardial Infarction: the Use of Coronary Angioplasty and the Integration of the New Support Device into Patient Management, GM Gacioch, MD; Stephen G. Ellism, MD, FACC; L Lee, MD; ER Bates, MD, FACC; M Kirsh, MD, FACC; JA Walton, MD, FACC; EH Topol, MD, FACC, Journal of the American College of Cardiology, vol. 19, No. 3, Mar. 1, 1992.

Reoperative Coronary Artery Bypass Grafting Without Cardiopulmonary Bypass, WJ Fanning, MD; GS Kakos, MD; and TE Williams, Jr., MD, Ph.D., The Annals of Thoracic Surgery, vol. 55, No. 2, Feb. 1993, pp. 486-489.

Enhanced Preservation of Acutely Ischemic Myocardium with Transeptal Left Ventricular Assist, JD Fonger, MD; Y Zhou, MD; H Matsuura, MD; GS Aldea, MD; and RJ Shemin, MD, The Annals of Thoracic Surgery, vol. 57, No. 3, Mar. 1994, pp. 570-575.

Transcatheter Radiofrequency Ablation of Atrial Tissue Using a Suction Catheter, Th Lavergne et al. (PACE, vol. 12, Jan. 1989, Part II, pp. 177-186.

Abstract: "Closed Chest Coronary Artery Bypass With Cardioplegic Arrest in the Dog", Stevens et al. 67th Scientific Sessions.

Placement of Coronary Artery Bypass Graft without Pump Oxygenator, Trapp et al., Journal of The Society of Thoracic Surgeons and The Southern Thoracic Surgical Assn. vol. 19. No. 7 Jan. 1975.

Experimental Videothoracoscopic Cannulation of the Left Atrial Appendix: A Feasible Rapid Approach For Initiating Left Heart Bypass? PF Grundeman; DW Meijer; JJG Bannenberg; R tukkie; and PJ Klopper, Surgical Endoscopy (1993) 7: 511-513.

A.J. Delrossi, M.D., and G.M. Lemore, M.D., A New Retractor to Aid In Coronary Artery Surgery, The Annals of Thoracic and Cardiovascular Surgery, vol. 36 Jul. 1983 pp. 101-102.

Stephen Westaby, FRCS, and Federico J. Benetti, MD, Less Invasive Coronary Surgery: Consensus From the Oxford Meeting, Annals of Thoracic Surgery 1996; 62: 924-31.

Kolessov V.I., The Surgery of Coronary Arteries of the Heart, Leningrad, Meditsina, 1977, pp. 360. (Russian Article).

Kosesssov V.I., The Surgery Of Coronary Arteries of the Heart, Leningrad, Meditsina., 1977, pp. 360. (English Translation).

Reexam Control No. 90/005,995, dated May 3, 2001.

Reexam Control No. 90/005,994, dated May 3, 2001.

* cited by examiner

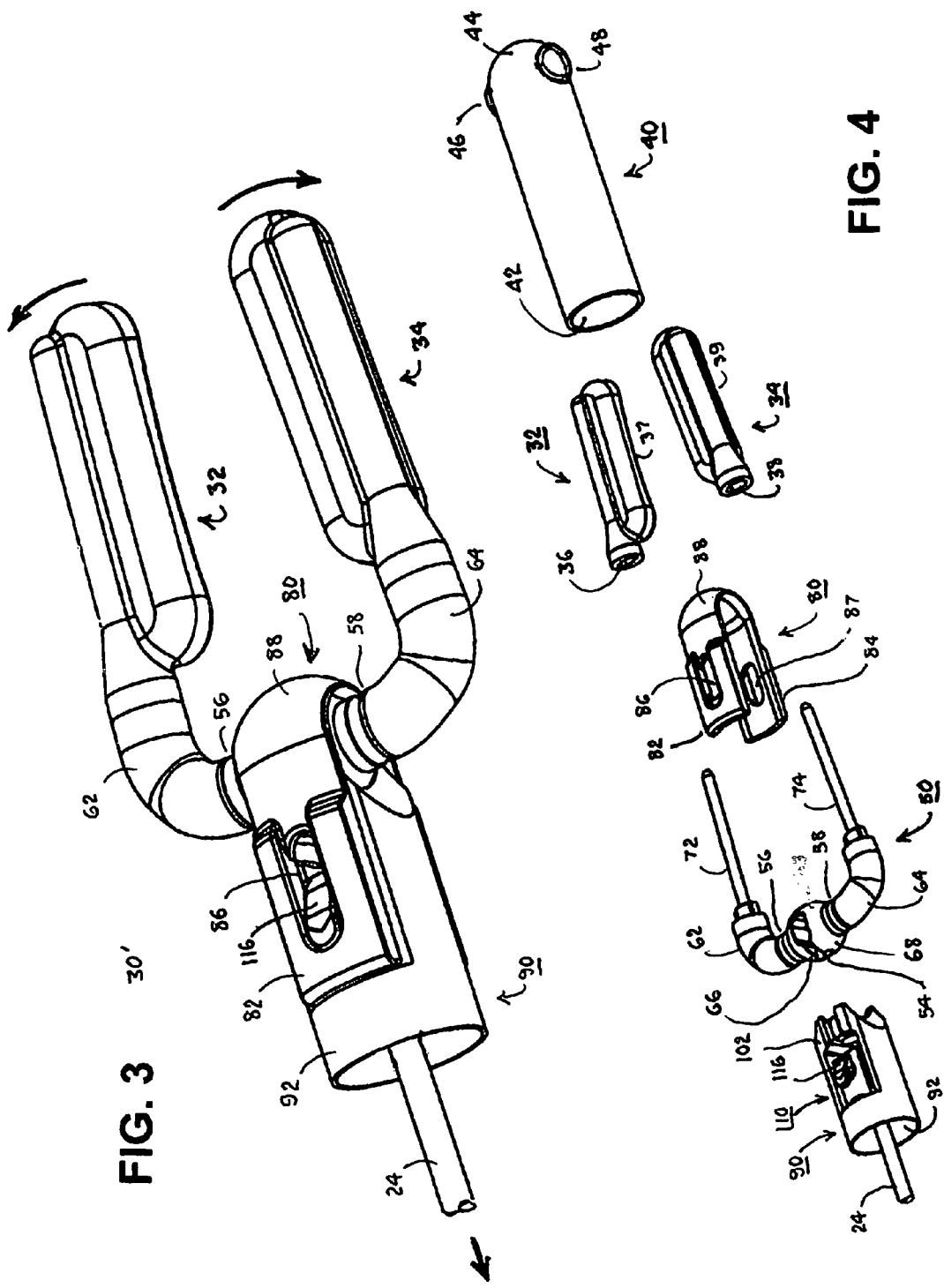

METHODS AND APPARATUS PROVIDING SUCTION-ASSISTED TISSUE ENGAGEMENT

REFERENCE TO RELATED PENDING PATENT APPLICATIONS

Reference is hereby made to commonly assigned, co-pending U.S. patent application Ser. No. 10/643,299 filed Aug. 19, 2003, entitled METHOD AND SYSTEM FOR ORGAN POSITIONING AND STABILIZATION in the names of Philip J. Haarstad et al and U.S. patent application Ser. No. 10/675,815 filed Sep. 30, 2003, entitled METHODS AND APPARATUS PROVIDING SUCTION-ASSISTED TISSUE ENGAGEMENT THROUGH A MINIMALLY INVASIVE INCISION in the names of Philip J. Haarstad et al.

FIELD OF THE INVENTION

This invention relates generally to suction-assisted tissue-engaging devices, systems and methods that can be employed to engage, i.e., position, manipulate, stabilize, and/or hold tissue, e.g., tissue of a body organ, during a medical procedure through a suction member or head applied to the tissue, particularly to apply suction to the heart to engage and position, manipulate, stabilize, and/or hold the beating heart during cardiac surgery.

BACKGROUND OF THE INVENTION

Coronary artery disease remains the leading cause of morbidity and mortality in Western societies. Coronary artery disease is manifested in a number of ways. For example, disease of the coronary arteries can lead to insufficient blood flow to various areas of the heart. This can lead to the discomfort of angina and the risk of ischemia. In severe cases, acute blockage of coronary blood flow can result in irreversible damage to the myocardial tissue including myocardial infarction and the risk of death.

A number of approaches have been developed for treating coronary artery disease. In less severe cases, it is often sufficient to merely treat the symptoms, with pharmaceuticals, or treat the underlying causes of the disease, with lifestyle modification. In more severe cases, the coronary blockage can be treated endovascularly or percutaneously using techniques such as balloon angioplasty, atherectomy, laser ablation, stents, and the like.

In cases where these approaches have failed or are likely to fail, it is often necessary to perform a coronary artery bypass graft (CABG) procedure. CABG surgery, also known as "heart bypass" surgery, generally entails the use of a graft or conduit to bypass the coronary obstruction and, thereby provide blood flow to the downstream ischemic heart tissues. The major objective of any CABG procedure is to perform a technically perfect anastomosis of the graft with the vessel. Creation of a technically perfect anastomosis is generally complex, tedious, time consuming and its success is highly dependent on a surgeon's skill level.

The CABG procedure is typically conducted on an arrested heart while the patient is on a cardiopulmonary bypass (CPB) circuit, also known as a "heart-lung machine" that provides continuous systemic blood circulation, while cardioplegic cardiac arrest enables meticulous anastomosis suturing in a bloodless, still-heart, operating field. In a CPB procedure performed as an adjunct to a CABG procedure, the patient's venous blood that normally returns to the right atrium is diverted to a CPB system or circuit that supplies oxygen to the blood and removes carbon dioxide from the blood and returns the blood, at sufficient pressure, into the patient's aorta for further distribution through the arterial system to the body. Creation of the CPB circuit typically entails arterial and venous cannulation, connecting the bloodstream to a heart-lung machine, cooling the body to about 32° Celsius, cross clamping of the aorta, and cardioplegic perfusion of the coronary arteries to arrest and cool the heart to about 4° Celsius. The arrest or stoppage of the heart is generally required because the constant pumping motion of the beating heart would make surgery upon the heart difficult in some locations and extremely difficult if not impossible in other locations. Generally, such a CPB system requires several separate components, including an oxygenator, several pumps, a reservoir, a blood temperature control system, filters, and flow, pressure and temperature sensors.

A blood vessel or vessels for use in the graft procedure are harvested or mobilized from the patient. In the majority of patients, obstructed coronary arteries are bypassed using an in situ internal mammary artery (IMA) or a reversed segment of saphenous vein harvested from a leg although other graft vessels may also be used. For this reason, CABG surgery is typically performed through a median sternotomy, which provides access to the heart and to all major coronary branches. A median sternotomy incision begins just below the sternal notch and extends slightly below the xiphoid process. A sternal retractor is used to spread the left and right rib cage apart for optimal exposure of the heart. Hemostasis of the sternal edges is typically obtained using electrocautery with a ball-tip electrode and a thin layer of bone wax. The pericardial sac is opened thereby achieving direct access to the heart. One or more grafts are attached to the relevant portion of a coronary artery (or arteries) to bridge the obstruction while the heart is in cardiac arrest. Then, the patient is weaned from CPB, the heart is restarted, and cannulation is discontinued. The surgical incisions in the chest are then closed.

The CABG procedure is generally expensive, lengthy, traumatic and subject to patient risk. The arrest of the heart and the use of the CPB circuit add to the time and expense of the CABG procedure and present a number of risk factors to the patient. The initiation of global (hypothermic) cardiac arrest may result in global myocardial ischemia, and cross clamping the ascending aorta may contribute to the patient experiencing a post-operative stroke. In fact, recent studies have shown aortic clamping and manipulation may release atherosclerotic debris into the bloodstream, resulting in neurological injury. Exposure of blood to foreign surfaces results in the activation of virtually all the humoral and cellular components of the inflammatory response, as well as some of the slower reacting specific immune responses. A systemic inflammatory response can result due to the interactions of blood elements with the artificial material surfaces of the components of the CPB circuit. Other complications associated with cardiopulmonary bypass include loss of red blood cells and platelets due to shear stress damage. In addition, cardiopulmonary bypass requires the use of an anticoagulant, such as heparin that increases the risk of hemorrhage. Cardiopulmonary bypass also sometimes necessitates giving additional blood to the patient that may expose the patient to blood-borne diseases, if it is from a source other than the patient. Therefore, a number of cardiac surgical procedures have been developed or proposed to enable off-pump, beating heart, CABG procedures either through a median sternotomy or employing minimally invasive procedures and even totally endoscopic procedures with access through ports extending through the chest wall into the thoracic cavity.

In one approach, pressure is applied against at least a portion of the heart to stabilize it and facilitate CABG or beating heart procedures as exemplified by the stabilization apparatus disclosed in U.S. Pat. Nos. 5,875,782, 6,120,436, and 6,331,158, for example. In one embodiment disclosed in the '436 patent, a U-shaped platform is pressed against the heart surface exposed through a thoracotomy and maintained there by suturing the platform to the myocardium or by attaching the platform to the end of an adjustable arm. The adjustable arm is mounted to a sternal retractor frame maintaining the ribs spread apart, and the adjustable arm can be adjusted to direct pressure through the platform against the heart to stabilize it. In addition, mechanical systems for lifting the heart, particularly to enable access to the heart for performing valve surgery, have been proposed as exemplified in the apparatus disclosed in U.S. Pat. No. 6,558,318.

In another approach, suction is applied to the epicardium of the heart to stabilize an area of the heart. Typically, an elongated shaft is coupled to a distal suction member, and a vacuum is drawn through a lumen of an elongated shaft or a vacuum line to apply suction to the epicardium to grasp and stabilize it. Suction-assisted tissue-engaging devices for cardiac surgery having circular or horseshoe-shaped suction members introduced through a sternotomy are disclosed in U.S. Pat. Nos. 5,727,569, 5,782,746, 6,071,295, and 6,602,183 and in U.S. Patent Application Publication 2002/0045888, for example. In certain cases, flexible suction tubes or vacuum lines extend from each suction member to an operating room vacuum source. The vacuum lines are bonded to elongated shafts of a forceps type device shown in certain forceps embodiments or the '569 patent. In other cases, a vacuum is drawn through one or more suction lumen within the rigid shaft of the suction application device coupled to the suction member.

Early versions of the Medtronic® Octopus™ tissue stabilizer used to apply suction to and thereby stabilize a site of the beating heart are disclosed in commonly assigned U.S. Pat. Nos. 6,464,630 and 6,394,948, for example. In certain embodiments, the tissue stabilizer employs a single elongated suction pod fixed at the distal end of an elongated shaft to extend substantially axially and distally to the elongated shaft distal end. It is necessary to employ two such elongated shafts and suction pods to place the suction pads on either side of the heart surface to be stabilized. In the schematically depicted embodiment of FIG. 33 of the '948 patent, the distal suction member comprises a horseshoe-shaped suction pod extending from the shaft distal end. In these embodiments, the shaft is malleable to shape it so as to apply the suction pod against the heart tissue at the site. A vacuum is drawn through a lumen of the shaft to apply suction at the suction ports of the suction pod.

Various current models of the Medtronic® Octopus tissue stabilizer and/or Medtronic® Starfish™ heart positioner and accessories, both available from the assignee of the present invention, have improved articulating arms supporting distal suction members. The Medtronic® Octopus 3™ tissue stabilizer is approved for use in applying suction to a surface of the heart to stabilize the heart tissue at the site of engagement while the heart is beating to facilitate a surgical procedure, e.g., to perform an anastomosis in the course of a CABG procedure. The Medtronic® Starfish™ heart positioner is approved for use in applying suction to a surface of the heart, particularly near the apex of the heart, to move and reposition the heart to achieve better access to areas that would otherwise be difficult to access, such as the posterior or backside of the heart. For example, the surgeon can bring an anastomosis site into better view by supporting and rotating the heart using the Starfish™ heart positioner. The surgeon can also use the Octopus 3™ tissue stabilizer in the same procedure to stabi-lize the anastomosis site. See, for example, commonly assigned U.S. Pat. Nos. 5,836,311, 5,927,284, 6,015,378, 6,464,629, and 6,471,644, and European Patent Publication No. EP 0 993 806 describing aspects of the Octopus 3™ heart stabilization system, commonly assigned U.S. Patent Application Publication U.S. 2002/0095067 disclosing aspects of the Starfish™ heart positioner, and commonly assigned U.S. Patent Application Publication U.S. 2002/013809 disclosing use of both in the same surgical procedure.

The Octopus 3™ tissue stabilizer and the Starfish™ heart positioner are both provided with an elongated articulating arm that extends between a proximal clamp and a distal suction member. These suction-assisted, tissue-engaging devices are used in open chest sternotomy procedures that involve making a 20 to 25 cm incision in the chest of the patient, severing the sternum, cutting and peeling back various layers of tissue in order to give access to the heart and arterial sources, and fitting a sternal retractor frame extending across the incision to maintain the ribs spread apart. The clamps at the proximal ends of the articulating arms of the Medtronic® Octopus 3™ tissue stabilizer and Starfish™ heart positioner can be mounted to the Medtronic® Octo-Base™ sternal retractor.

The elongated articulating arms of the Octopus 3™ tissue stabilizer and the Starfish™ heart positioner each comprise a plurality of articulating links strung over an internal cable that extends between the suction member and a proximal knob adjacent the proximal clamp. The proximal knob attached to the cable proximal end can be rotated in a cable tightening direction to stiffen and maintain a shape of the articulating support arm or in the opposite, cable loosening direction to relax the articulating support arm. Each articulating link has opposite ends, one of which is concave and the other of which is convex (e.g., hemispherical). The convex end of one articulating link fits into the concave end of the adjacent articulating link and allows the articulating links to articulate relative to one another if the central cable has not been tensioned to lock the articulating links together. The articulating links are encased within the lumen of a flexible sheath to prevent ingress of body fluids or tissue that might interfere with the articulation of the links.

The distal link is coupled to a suction member that is separately coupled to a flexible tube or vacuum line that is adapted to extend to and be coupled to a vacuum source in the operating room for applying suction to the heart when suction ports of the suction member are applied against the heart. In use, the proximal knob is rotated in the cable loosening direction to release tension on the cable so that a curve or bend can be shaped along the length of the support arm by manipulating the articulating links to dispose the suction member against the epicardium. The proximal knob can then be rotated in the tightening direction to tension the cable, thereby drawing the articulating links together to lock them together in a locked condition that maintains the shape.

The suction member of the Octopus 3™ tissue stabilizer comprises a pair of elongated, malleable, stabilizer pods that are coupled to the distal link to extend in a U-shape, side by side and distally of the distal link. Vacuum lines are coupled to each stabilizer pod, and suction is applied through a plurality of ports of each stabilizer pod. The stabilizer pods are supported by a spreading mechanism extending from the distal link that is indirectly coupled to the tensioning cable. As described in the above-referenced '629 patent, the physician can manually shape the articulating arm to dispose the suction ports of the stabilizer pods against the epicardium, provide suction through the suction lines to grasp the epicardium, and then rotate the proximal knob to tension the cable. The tensioning of the cable concurrently causes the articulating arm to become rigid and the stabilizer pods to spread apart, thereby stabilizing the myocardium between the stabilizer pods while the heart continues to beat.

The Starfish™ heart positioning system employs a three appendage, silicone head mounted to the distal end of a malleable, articulating arm. The silicone head is shaped so that the flexible appendages or legs diverge apart and can engage the heart surface particularly adjacent to the apex of the heart to lift and position the heart when suction is applied. In use, the physician lifts the heart, shapes the articulating arm to apply the three appendages about the apex, provides suction through the suction line to grasp the epicardium, and then rotates the proximal knob in the tensioning direction to tension the cable and make the articulating arm rigid.

Further suction-assisted tissue-engaging devices for use in cardiac surgery through a sternotomy employing articulating arms coupled to distal suction members that are in turn coupled to vacuum lines are disclosed U.S. Pat. No. 6,210,323 and in PCT Publication WO 01/17437 A2.

Surgeons have found that the Octopus 3™ stabilization system and Starfish™ heart positioner provide significant benefits in the above-described operative procedures involving relatively large sternotomies or thoracotomies. However, the vacuum line or lines extending from the suction members coupled to the distal end of the articulating arm can at times be inconvenient and obstruct the view or access in the operative field typically defined by the sternal retractor frame. It would be desirable to be able to enjoy the advantages of such suction-assisted, tissue-manipulation systems employing articulating arms without having vacuum lines extending from the distal suction members.

SUMMARY OF THE INVENTION

In accordance with the present invention, suction-assisted tissue-engaging devices, systems, and methods are provided that can be employed through a surgical incision to engage body tissue, e.g., tissue of an organ, during a medical procedure through application of suction to the tissue through a suction member of a suction-assisted tissue-engaging device applied to the body tissue, particularly to the epicardium of the heart to stabilize or position the heart.

The suction-assisted tissue-engaging device of the present invention further comprises an elongated articulating arm extending between an articulating arm proximal end and an articulating arm distal end supporting a suction member having suction ports. An arm vacuum lumen extends through the articulating support arm from a proximal vacuum port to a suction member vacuum lumen extending to the suction ports. The arm proximal end preferably comprises a mechanism that can be attached to and detached from a fixed reference point with respect to the body tissue to be grasped. The articulating arm can be manipulated in shape while in a flexible condition or state and maintains the shape in a rigid condition or state.

In preferred embodiments, the articulating arm is formed of a plurality of interlocking articulating links within an outer sheath lumen of a flexible outer sheath and an elongated tensioning cable extending through aligned articulating link bores. A distal articulating link and the tensioning cable distal end are coupled to a component or components of the suction member. The tensioning cable proximal end is coupled to a tensioning mechanism for selectively applying tension to the tensioning cable to draw the articulating links together and render the articulating arm rigid and releasing tension from the tensioning cable to separate the articulating links and render the articulating arm flexible. The arm vacuum lumen extends alongside the tensioning cable.

A vacuum port is provided into the arm vacuum lumen distal to the tensioning mechanism and a vacuum seal is provided between the vacuum port and the tensioning mechanism. The vacuum seal seals against the tensioning cable as the tensioning mechanism is operated to change the flexible state to a sealed state intermediate the flexible state and the rigid state. Advantageously, the articulating arm can be manipulated in shape while in a flexible sealed state.

In one preferred embodiment, the distal suction member comprises a pair of distally extending stabilizer pods having suction ports adapted to be applied against body tissue. The stabilizer pods are mounted to be spread apart when the tensioning mechanism is operated to render the articulating arm rigid.

In use in relation to the exposed heart, the articulating arm is manipulated while in the flexible state to apply the suction ports of the distal stabilizer pods against the epicardium. Tension is applied to the tensioning cable through operation of the tensioning mechanism to seal the vacuum seal against the tensioning cable. Vacuum is then applied to the vacuum port, and suction is applied to the epicardium through suction ports of the distal stabilizer pods via the vacuum lumens of the articulating arm and components of the suction member. Further tension applied to the tensioning cable causes the articulating arm to become rigid and the distal stabilizer pods to spread apart and immobilize the myocardium between the distal stabilizer pods.

In a further preferred embodiment, the distal suction member comprises a suction pad having three flexible appendages or legs having suction ports adapted to be applied against the epicardium at or near the apex of the heart.

In use in relation to the exposed heart, the articulating arm is manipulated while in the flexible state to apply the suction ports of the distal suction pad against the epicardium. Tension is applied to the tensioning cable through operation of the tensioning mechanism to seal the vacuum seal against the tensioning cable. Vacuum is then applied to the vacuum port, and suction is applied to the epicardium through suction ports of the flexible legs via the vacuum lumens of the flexible legs and components of the suction member and further tension is applied to the tensioning cable to render the articulating arm rigid.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 3 is a perspective view of a suction member sub-assembly (without the distal sealing sleeve) and a distal portion of the tensioning cable of FIG. 1;

FIG. 4 is a perspective exploded view of the components of the suction member of FIGS. 1 and 3 including two stabilizer pods, an insert mold assembly, a sling, a head link, a cable tab, a distal sealing sleeve, and a distal segment of the tensioning cable;

DETAILED DESCRIPTION OF THE INVENTION

Figure 1:
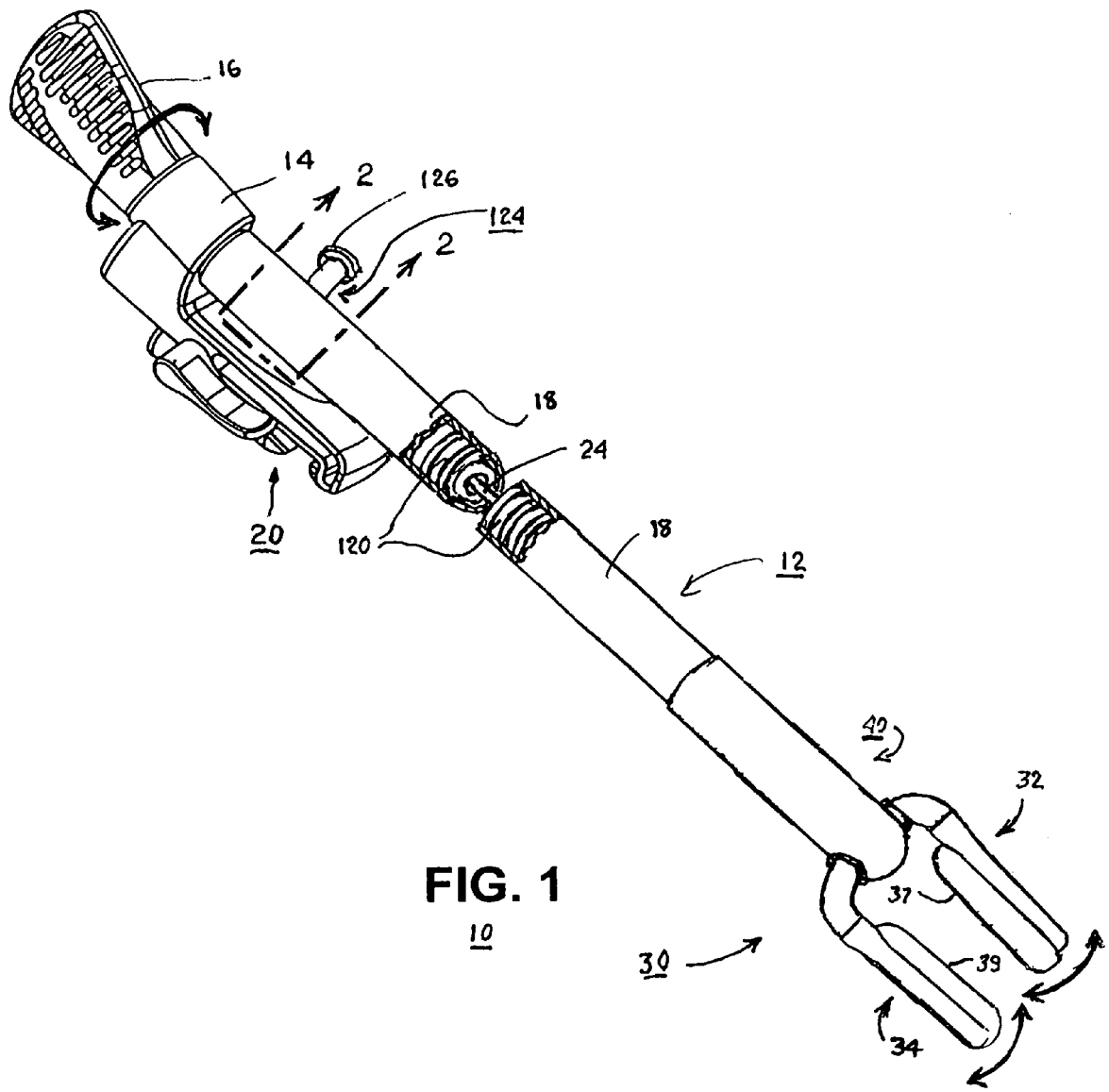
FIG. 1 is a perspective view of a first preferred embodiment of a suction-assisted, tissue-engaging device comprising an elongated articulating arm extending between a proximal knob and a distal suction member comprising a pair of distally extending stabilizer pods.

In the following detailed description, references are made to illustrative embodiments of methods and apparatus for carrying out the invention. It is understood that other embodiments can be utilized without departing from the scope of the invention. Preferred methods and apparatus are described for accessing the heart surface in the thoracic cavity and stabilizing or positioning the heart as an example of accessing an anatomic space or cavity containing body tissue to stabilize or position the tissue to perform a medical procedure.

The term "medical procedure" may mean any one or more medical or surgical procedures such as, for example cardiac surgery, performed with or without CPB, heart valve repair, heart valve replacement, MAZE procedures, transmyocardial revascularization (TMR), CABG procedures, anastomosis procedures, non-surgical procedures, endoscopic procedures, non-invasive procedures, invasive procedures, port-access procedures, fluoroscopic procedures, beating heart surgery, vascular surgery, neurosurgery, electrophysiology procedures, diagnostic and therapeutic procedures, ablation procedures, ablation of arrhythmias, endovascular procedures, treatment of one or more organs and/or vessels, treatment of the heart, aneurysm repair, aortic aneurysm repairs, imaging procedures of the heart and great vessels, CAT scan procedures, MRI procedures, cardiograms, pharmacological therapies, drug delivery procedures, delivery of biological agents, gene therapies, cellular therapies, cancer therapies, radiation therapies, genetic, cellular, tissue and/or organ manipulation or transplantation procedures, coronary angioplasty procedures, placement or delivery of coated or uncoated stents, LVAD procedures, lead placement procedures, placement of cardiac reinforcement devices, placement of cardiac assistance devices, atherectomy procedures, atherosclerotic plaque manipulation and/or removal procedures, emergency procedures, cosmetic procedures, reconstructive surgical procedures, biopsy procedures, autopsy procedures, surgical training procedures, birthing procedures, congenital repair procedures, and medical procedures that require positioning one or more organs and/or tissues.

One preferred embodiment of the suction-assisted tissue-engaging device 10 of the present invention is depicted in FIGS. 1-9 and 12 and comprises an elongated articulating arm 12 extending between a proximal clamp 20 and tensioning knob 16 and a distal suction member 30. The articulating arm 12 comprises an outer sheath 18 that extends from an outer sheath 40 of the distal suction member 30 to a clamp fitting 14 of the clamp 20. In accordance with the present invention, a vacuum is drawn from suction ports 37 and 39 of distally extending stabilizer pods 32 and 34 through the articulating arm 12 by a vacuum source coupled to a vacuum port 124.

Figure 12:
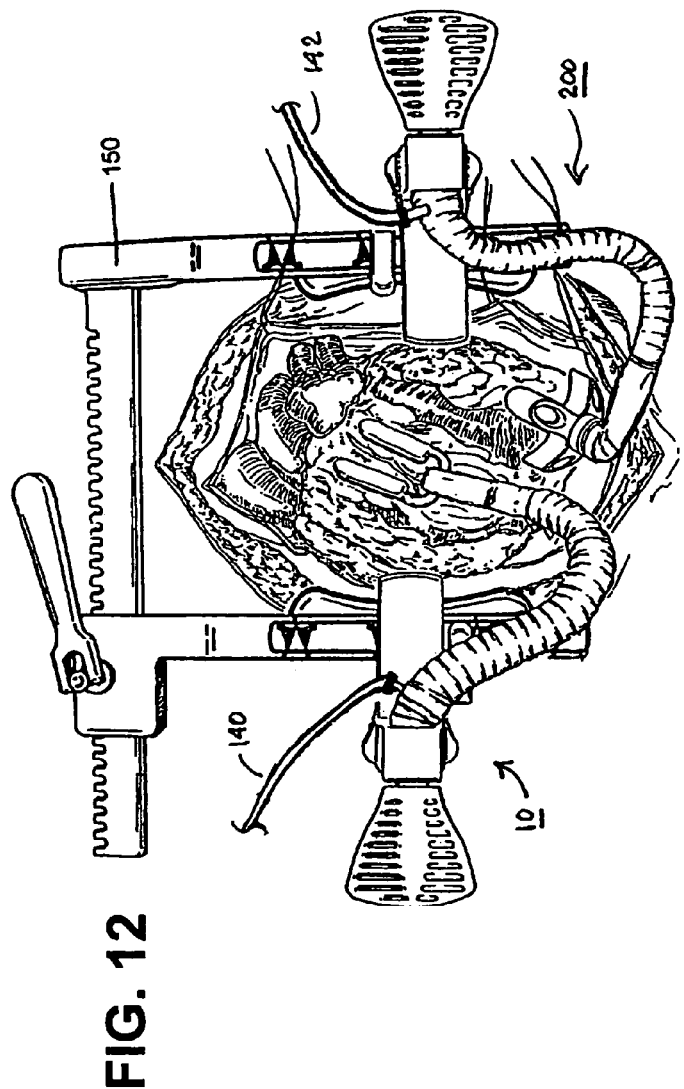
FIG. 12 is a plan view illustrating the first and second preferred embodiments of the suction-assisted, tissue-engaging device clamped to a sternal retractor and in use stabilizing and lifting a surgically exposed heart.

The suction-assisted, tissue-engaging devices of the present invention are used in open chest sternotomy procedures that involve making a 20 to 25 cm incision in the chest of the patient, severing the sternum, cutting and peeling back various layers of tissue in order to give access to the heart and cardiac vessels, and fitting the frame of a sternal retractor 150 extending across the incision. The exemplary clamp 20 at the proximal end of the articulating arm 12 depicted in FIG. 1 can be mounted to a sternal retractor 150, e.g., the Medtronic® OctoBase™ sternal retractor, as shown in FIG. 12, to maintain the ribs spread apart. The components and operation of the clamp 20 may correspond to those described in the above-referenced, commonly assigned '769 patent, particularly with reference to FIG. 3 thereof.

Figure 2:
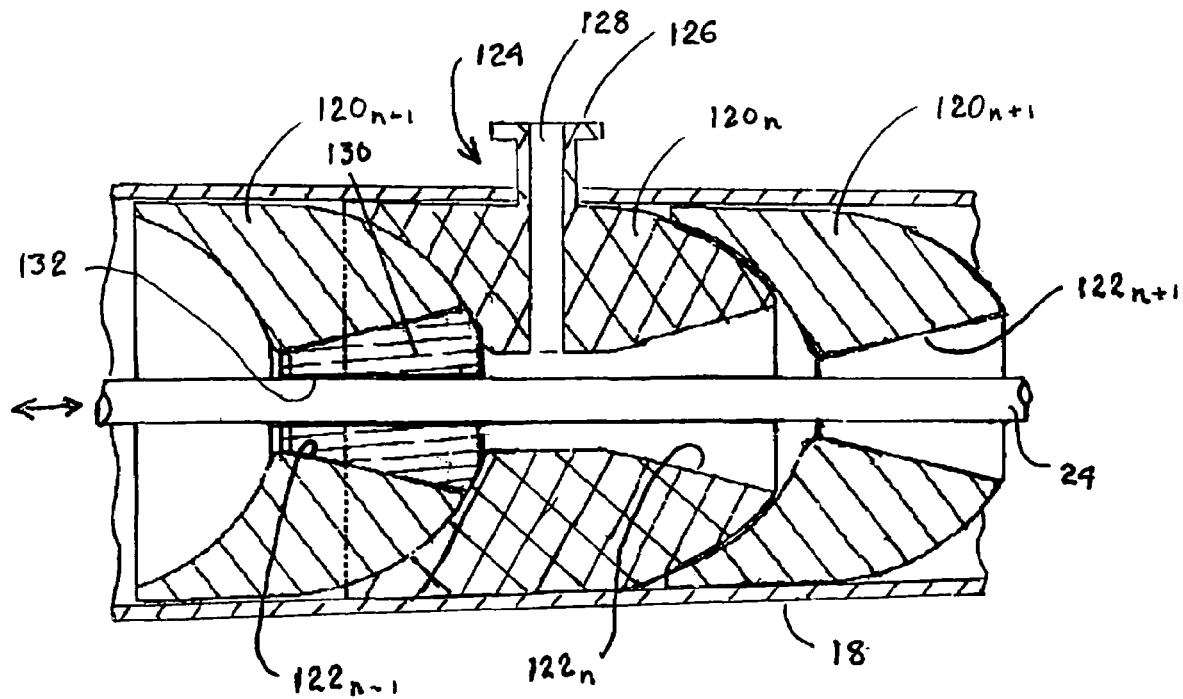
FIG. 2 is a cross-section view taken along lines 2-2 of FIG. 1 depicting a vacuum port into the articulating arm adapted to be coupled to a vacuum source and a distal seal for sealing the arm vacuum channel of the articulating arm.

As shown in FIGS. 1 and 2, a plurality of articulating links 120 are strung over a flexible tensioning cable 24 that extends between a distal cable ball 26 (shown in FIG. 4) and a proximal connection with the tensioning knob 16. The articulating links 120 each having a link proximal end and a link distal end and a link bore 122 extending between the link proximal and distal ends, the link proximal and distal ends of adjacent articulating links shaped to provide end-to-end articulation with the link bores aligned. Each articulating link 120 has opposite concave and convex (e.g., hemispherical) link ends and a central link bore 122 that the cable 24 extends through. The convex end of one articulating link 120 fits into the concave end of the adjacent articulating link 120 with the tensioning cable 24 extending through the central link bore 122. The mating concave and convex link ends allow the articulating links 120 to articulate relative to one another in a "ball and socket" fashion as long as the tensioning cable 24 is not tensioned to lock the articulating links 120 together as described in detail in the above-referenced, commonly assigned '629 patent, particularly in reference to FIGS. 1A-1F thereof. The central link bore 122 of each articulating link 120 is conical and somewhat larger in diameter at its minimum diameter than the diameter of the tensioning cable 24. The articulating links 120 and tensioning cable 24 are encased within the lumen of the flexible outer sheath 18 to prevent ingress of body fluids or tissue that might interfere with the articulation of the links 120. In accordance with the present invention, a vacuum is also drawn through an arm vacuum lumen within the flexible outer sheath lumen between the tensioning cable 24 and the bores 122 of the articulating links 120.

The proximal tensioning knob 16 is rotated in the cable loosening direction to release tension on the tensioning cable 24 so that a curve or bend can be shaped along the length of the articulating arm 12 by manipulating the articulating links 120 within the outer sheath 18 to dispose the suction ports 37 and 39 of stabilizer pods 32 and 34 against the epicardium as shown in FIG. 12. The proximal tensioning knob 16 can then be rotated in the tightening direction to tension the cable 24, thereby drawing the articulating links 120 together to lock them into a shaped position. The proximal tensioning knob 16 can be further rotated in the tightening direction to pull the distal cable ball 26 proximally causing the stabilizer pods 32 and 34 to spread apart as shown in FIGS. 1 and 3. The particular details of the proximal tensioning knob 16 and its connection to the cable proximal end are described in the above-referenced, commonly assigned '769 patent, particularly with reference to FIG. 3 thereof.

In accordance with one aspect of the present invention, the vacuum port 124 is formed as a part of a modified non-articulating link or articulating link distal to the proximal tensioning knob 16. As described further below, the selected articulating or non-articulating link does need to be able to move axially over the tensioning cable 24 upon rotation of the tensioning knob, but need not provide any appreciable articulation with adjacent proximal an distal links. A suitable non-articulating link could be disposed in the clamp fitting 14, but it is convenient to form the vacuum port 124 through an articulating link distal to the clamp fitting 14. Moreover, the modified non-articulating link or articulating link distal to the proximal tensioning knob 16 functions with a resilient seal having a seal bore and fitted into a seal seat of an articulating link or non-articulating link proximal to the modified non-articulating link or articulating link with the tensioning cable 24 extending through the seal bore.

Thus, in the exemplary embodiment shown in FIG. 2, the vacuum port 124 is depicted as part of an articulating link $120_n$ disposed intermediate a proximal (i.e., closer to tensioning knob 16) fixed or articulating link $120_{n-1}$, and a distal (i.e., closer to suction member 30) articulating link $120_{n+1}$. The vacuum port 124 depicted in detail in FIG. 2 comprises a vacuum port fitting 126 extending from the outer surface of articulating link $120_n$ through the outer sheath 18 and a link vacuum lumen 128 extending from a lumen end opening at the vacuum port fitting 126 through the vacuum port 124 and the side of the proximal articulating link $120_n$ into the central link bore $122_n$. The vacuum port 124 and vacuum port fitting 126 can include a stopcock and can take any convenient form that facilitates coupling with a flexible hose or vacuum line.

A resilient conical seal 130, preferably formed of resilient silicone rubber, having a seal bore 132 that the tensioning cable 24 extends through is fitted into the link central bore $122_{n-1}$ of the articulating link $120_{n-1}$ as shown in FIG. 2. Thus, the link central bore $122_{n-1}$ comprises a seal seat. The conical seal 130 is relaxed and expands within link central bore $122_{n-1}$ when the proximal tensioning knob 16 is rotated in the loosening direction so that the articulating links 120 along the length of the articulating arm 12 separate apart and can be manipulated into a suitable shape and the pods 32 and 34 of the suction member 30 can be applied against the epicardium. In this regard, the resilient seal 130 and resilient seal bore 132 are dimensioned with respect to the seal seat provided by link central bore $122_{n-1}$ and the tensioning cable 24 to compress the resilient seal 130 against the link central bore $122_{n-1}$ and the tensioning cable 24 as the tensioning cable 24 is drawn proximally to a sealed state intermediate the flexible state and the rigid state.

Thus, the conical seal 130 is progressively compressed between the link central bore $122_n$ of the articulating link $120_n$ and the mating convex end of the articulating link $120_{n-1}$ and against the tensioning cable 24 as the proximal tensioning knob 16 is rotated in the tightening direction. The initial stages of compression of the conical seal 130 between the link central bore $122_n$ of the articulating link $120_n$ decreases the vacuum leak from the arm vacuum lumen proximally sufficiently so that the vacuum may be applied through the vacuum port 124 before the articulating arm 12 is rendered fully rigid. The compressed conical seal 130 therefore prevents any loss of vacuum drawn through the vacuum port 124 proximally through the link central bores $122_n$, $122_{n-1}$, etc. The flexible outer sheath 18 prevents any loss of vacuum along the length of the articulating arm 12 distally from the vacuum port 124 that is drawn between the convex and concave mating ends of the articulating links 120. The articulating arm 12 in the sealed state can be further manipulated into a final operative state.

In use, a flexible hose or vacuum line 140 that extends to and is coupled to a vacuum source in the operating room that preferably provides a negative pressure of about 400 mm Hg is attached to the vacuum port fitting 126 as shown in FIG. 12. A stopcock (not shown) can be provided in the vacuum line 140 to provide or interrupt suction as necessary during the procedure. As described in the above-referenced '629 patent, the physician can manually shape the articulating arm 12 to dispose the suction ports 37 and 39 of the stabilizer pods 32 and 34 against the epicardium. The tensioning cable 24 is tightened sufficiently to compress the conical seal 130 about the tensioning cable 24 and into the seal seat. A vacuum is drawn through vacuum port lumen 128, the aligned central bores 122 of the articulating links 120 distal to the compressed conical seal 130 covered by the flexible outer sheath 18, and the vacuum channels of the distal suction member 30 for applying suction through the pod suction ports 37 and 39 to the epicardium. The physician can further manipulate the articulating arm 12 to a final operative shape. The physician then rotates the tensioning knob 16 further in the tightening direction to cause the stabilizer pods 32 and 34 to spread apart and to concurrently cause the articulating arm 12 to become rigid, thereby stabilizing the myocardium between the stabilizer pods 32 and 34 while the heart continues to beat.

The components of the distal suction member 30 depicted in FIGS. 3-9 comprise the cable ball 26 coupled to the distal end of the tensioning cable 24 (FIG. 8), the two stabilizer pods 32 and 34, and an outer sealing sleeve 40 (FIG. 4) overlying a spreading mechanism 52 of an insert mold assembly 50, a sling 80, a head link 90, and a cable tab 110 that are assembled together.

The elongated stabilizer pods 32 and 34 are formed of a malleable plastic material, e.g., a flexible PVC having pod lumens 36 and 38 communicating with internal vacuum channels that extend to a plurality of suction ports 37 and 39, e.g., four suction ports of each of the stabilizer pods 32 and 34, respectively. The suction ports 37 and 39 through the lower surfaces of the stabilizer pods 32 and 34, respectively, are preferably arranged in linear arrays that are somewhat offset from the axes of the lumens 36 and 38 following the teachings of the above-referenced commonly assigned '629 patent, particularly in reference to FIG. 1-F thereof. The proximal end openings of the pod lumens 36 and 38 are shaped to mate with keying elements of the insert mold assembly 50 as described below.

The outer sealing sleeve 40 is tubular having a sleeve lumen 42 extending from an open proximal end thereof to a closed, hemispheric, distal sleeve end 44. Sealing rings 46 and 48 are formed around laterally opposed openings through the sleeve sidewall proximal to the distal sleeve end 44. The sealing rings 46 and 48 comprise thickened opening edges or borders that are received in circumferential grooves 56 and 58, respectively, in the spreading mechanism 52 of the insert mold assembly 50 as described further below. The sleeve lumen diameter and the sealing ring diameters are selected so that the sleeve 40 snugly fits over the assembly of the sling 80 fitted over the spreading mechanism 52 of the insert mold assembly 50, the head link 90, and the cable tab 110 and a distal segment of the outer sleeve 18 that it is adhered to. The outer sealing sleeve 40 can thereafter accommodate movement of the components during rotation of the tensioning knob 16 in the tightening and loosening directions without losing its seal. The outer sealing sleeve 40 is preferably transparent so that the components and a trademark logo are visible through the sleeve.

Figure 5:
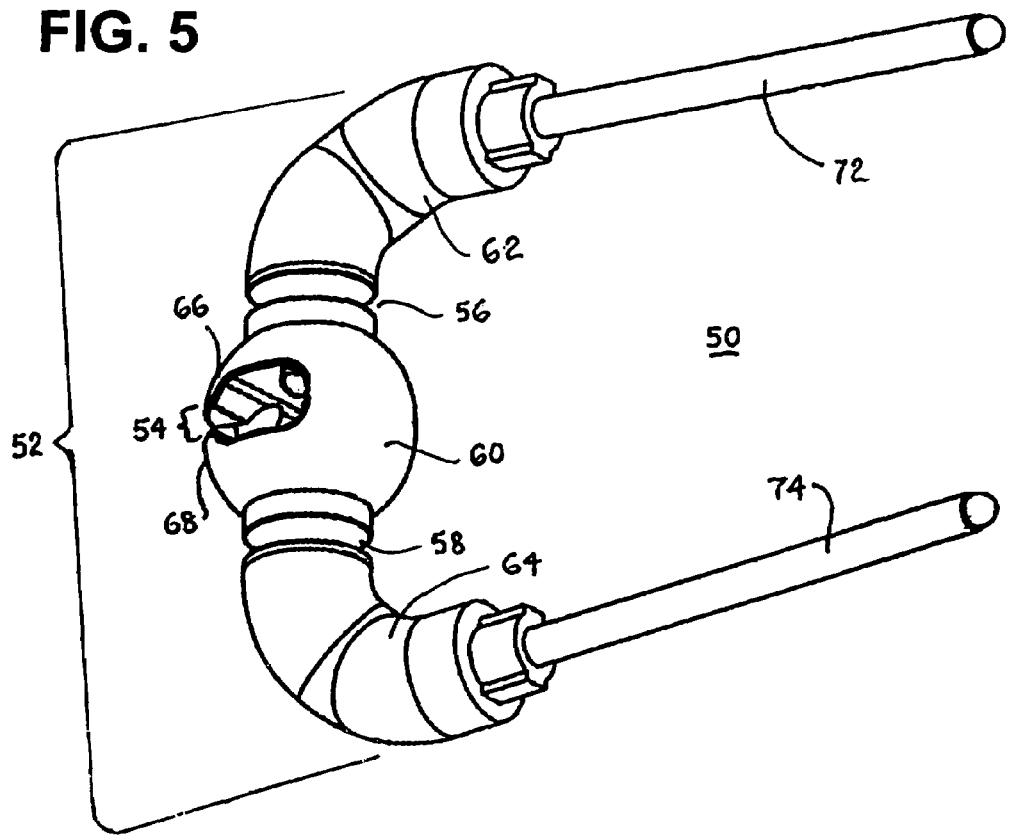
FIG. 5 is a perspective view of the U-shaped insert mold assembly of FIG. 4 comprising a split ball spreading mechanism and a pair of malleable tubes that support the stabilizer pods and through which a vacuum is drawn to provide suction at the suction ports of the stabilizer pods.

The U-shaped, insert mold assembly 50 shown in detail in FIG. 5 comprises a split ball spreading mechanism 52 molded of a relatively stiff plastic and a pair of malleable suction tubes 72 and 74. The split ball spreading mechanism 52 is insert molded in a mold forming the laterally extending arms 62 and 64 around intermediate segments of the generally L-shaped malleable suction tubes 72 and 74, respectively. The distal ends of the laterally extending arms 62 and 64 are keyed to mate with the shaped proximal end openings of the pod lumens 36 and 38.

The malleable suction tubes 72 and 74 can be formed of stainless steel hypotube, for example, having an outer diameter that is slightly smaller than the diameters of the pod lumens 36 and 38. The distal tube ends of the malleable suction tubes 72 and 74 are closed, but a plurality of vacuum holes (blocked from view in FIG. 5) through the tube sidewalls are spaced along the exposed distal segments of the malleable suction tubes 72 and 74. During assembly, the distal segments of the malleable suction tubes 72 and 74 are fitted into the pod lumens 36 and 38 respectively so that each vacuum hole through the sidewalls of the malleable suction tubes 72 and 74 is aligned with an internal vacuum channel of the stabilizer pods 32 and 34 that extends to one of the plurality of suction ports 37 and 39. Cement is applied between the mating surfaces to mechanically attach and prevent a vacuum leak at the junction, and the stabilizer pods 32 and 34 therefore cannot loosen and slip around the malleable suction tubes 72 and 74, respectively.

The laterally extending arms 62 and 64 of the split ball spreading mechanism 52 extend outward through substantially 90° elbows. The split ball spreading mechanism 52 is generally spherical or ball-shaped in the exposed outer surface between the laterally extending arms 62 and 64 thereby exhibiting a distal spherical surface 60. Sealing grooves 56 and 58 are formed around the laterally extending arms 62 and 64 that are dimensioned to receive and interference fit with the sealing rings 46 and 48, respectively, of the distal outer sleeve 40.

A proximal split or gap 54 is also molded extending distally toward the generally spherical proximal surface 60 to define proximal articulating surfaces 66 and 68 on either side of the proximal split 54 and to expose short proximal segments of the malleable suction tubes 72 and 74. The short proximal segments of the malleable suction tubes 72 and 74 extend into the proximal split 54 a slight distance.

Figure 9:
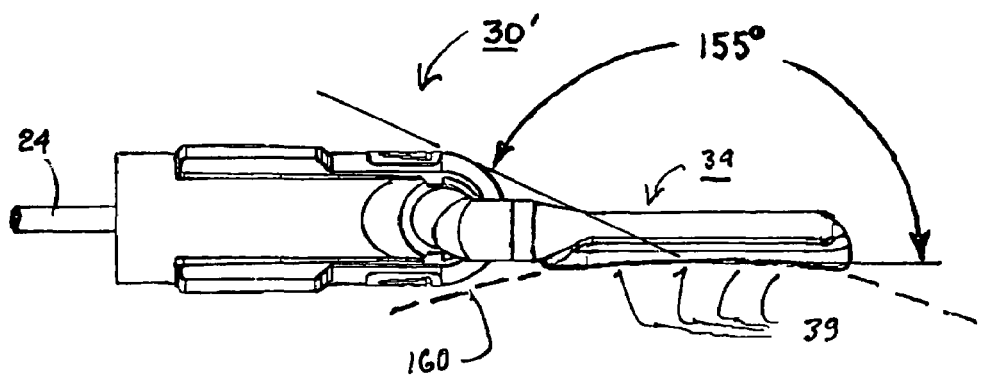
FIG. 9 is a side view of the suction member sub-assembly and distal segment of the tensioning cable of FIG. 3 illustrating the minimum angle of attack a range of motion of the stabilizer pods with respect to an epicardial surface.

The laterally extending arms 62 and 64 are molded around the intermediate segments of the malleable suction tubes 72 and 74, respectively, such that the laterally extending arms 62 and 64 are deflected downward slightly from the respective sealing grooves 56 and 58 as shown in FIG. 9. The downward, i.e., toward the epicardium 160, deflection of the laterally extending arms 62 and 64 disposes the axes of the respective malleable tubes 72 and 74 supporting the respective stabilizer pods 32 and 34 below, i.e., closer to the epicardium 160, than the axis of the suction member sub-assembly 30'. A maximum 155° field of view distal to the suction member sub-assembly 30' outer sealing sleeve 40 (not shown in FIG. 9 for convenience of illustration) is attained.

As described further below, the drawing of the tensioning cable 24 proximally applies compressive force between the distal spherical surface 60 and the proximal articulating surfaces 66 and 68 causing them to bend inward toward one another, diminishing the width of the split 54. The sling 80, head link 90, and cable tab 110 that are assembled together as depicted in FIG. 4 cooperate with the distal cable ball 26 and cable 24 to apply the compressive force when the tensioning cable 24 is drawn proximally by rotation of the proximal tensioning knob 16 in the tightening direction. The inward bending induces an outward spreading of the stabilizer pods 32 and 34 as indicated in FIGS. 1 and 3 in a manner similar to that described in the above-referenced, commonly assigned '629 patent, particularly in reference to FIGS. 10-21 thereof.

The sling 80 shown in FIG. 4 is formed of a relatively rigid plastic material and is shaped like a clip having somewhat arcuate lower and upper sling arms 82 and 84 joined at a generally spherical sling distal end 88. When assembled, the distal spherical surface 60 is nested against the inner surface of the sling distal end 88, like a ball in a sling. Tab openings 86 and 87 are formed through the lower and upper sling arms 82 and 84, respectively. A logo or other identifying indicia can be molded into the lower and upper sling arms 82 and 84 to be seen through the distal sleeve 40 following assembly as shown in FIG. 3.

Figure 6:
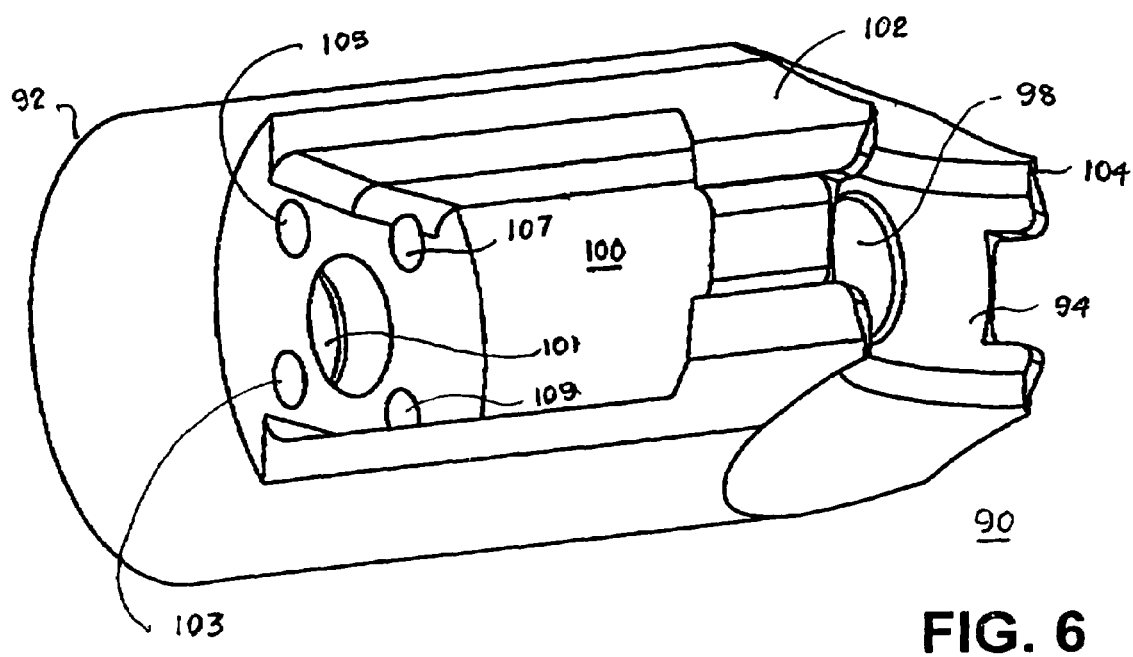
FIG. 6 is a perspective view of the distal head link of FIG. 4 that bears against the split ball and entraps the cable tab of FIG. 4 and a cable ball coupled to the cable distal end.

The head link 90 shown in detail in FIG. 6 is also formed of a relatively rigid plastic material and is generally tubular and extends between head link proximal end 92 and head link distal end 94. The proximal surface of the head link proximal end 92 is concave and mates with the distal convex end of the most distal link 120. A link cavity 100 is formed in the head link 90 intermediate the head link proximal and distal ends 92 and 94 that is shaped to receive the cable tab 110 with the cable ball 26 nested into the cable tab 110. The cylindrical outer surface of the head link 90 is also formed to provide opposed shaped sides 102 and 104 extending alongside and distal to the link cavity 100 to receive the lower and upper sling arms 82 and 84, respectively. The shaping provides that the assembly of the lower and upper sling arms 82 and 84 against the opposed sides 102 and 104 is substantially cylindrical, while the cable tab 110 and cable ball 26 are entrapped within the link cavity 100.

An oversize head link cable lumen 101 extends through the head link proximal end 92, whereby a vacuum can be drawn into the link cavity 100 through the clearance between the tensioning cable 24 and the head link cable lumen 101. A set of vacuum lumens 103, 105, 107, 109 through the head link distal end 94 extend into the link cavity 100. The opposed shaped sides 102 and 104 are shaped to provide vacuum channels between the lower and upper sling arms 82 and 84 and the opposed sides 102 and 104, respectively. The head link distal end 94 is shaped to provide a concave link force applying surface 96 that conforms in shape to the proximal articulating surfaces 66 and 68. A head link distal vacuum lumen 98 is also formed between the surface 96 and the head link cavity 100.

Figure 7:
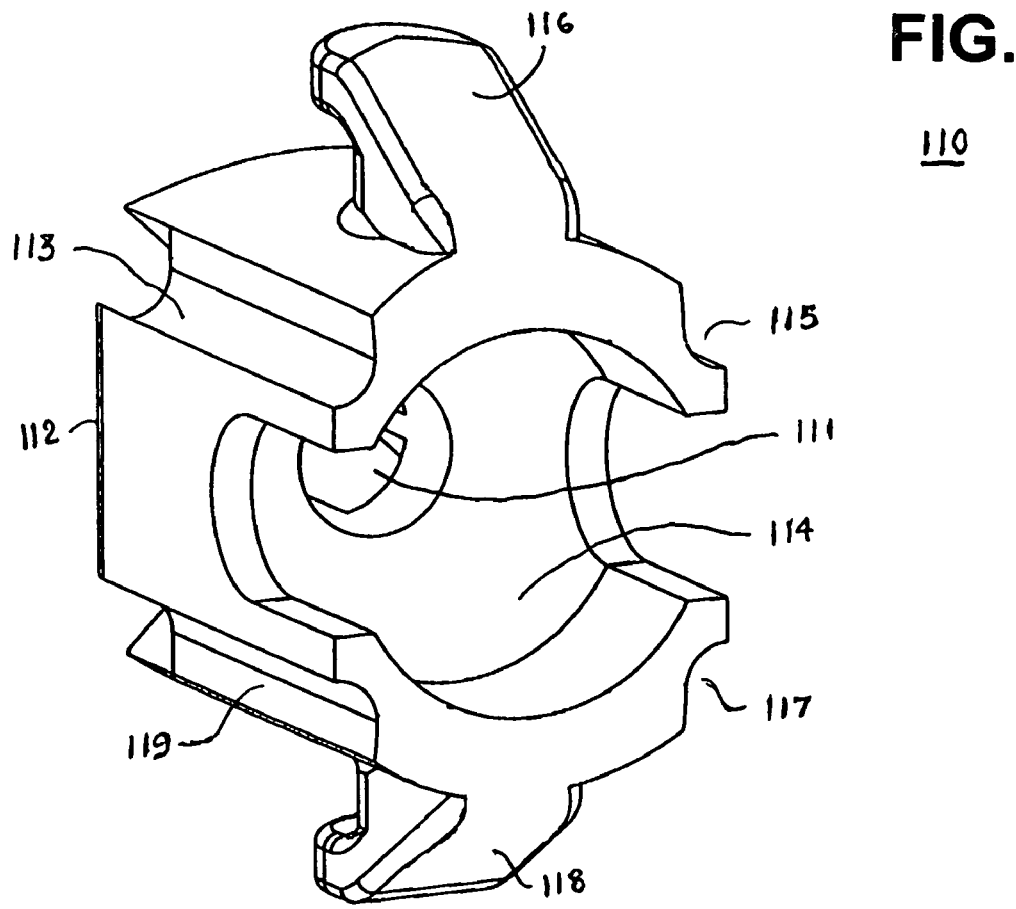
FIG. 7 is a perspective view of the cable tab of FIG. 4 that fits within the distal head link of FIG. 6 and receives a cable ball coupled to the cable distal end.
Figure 8:
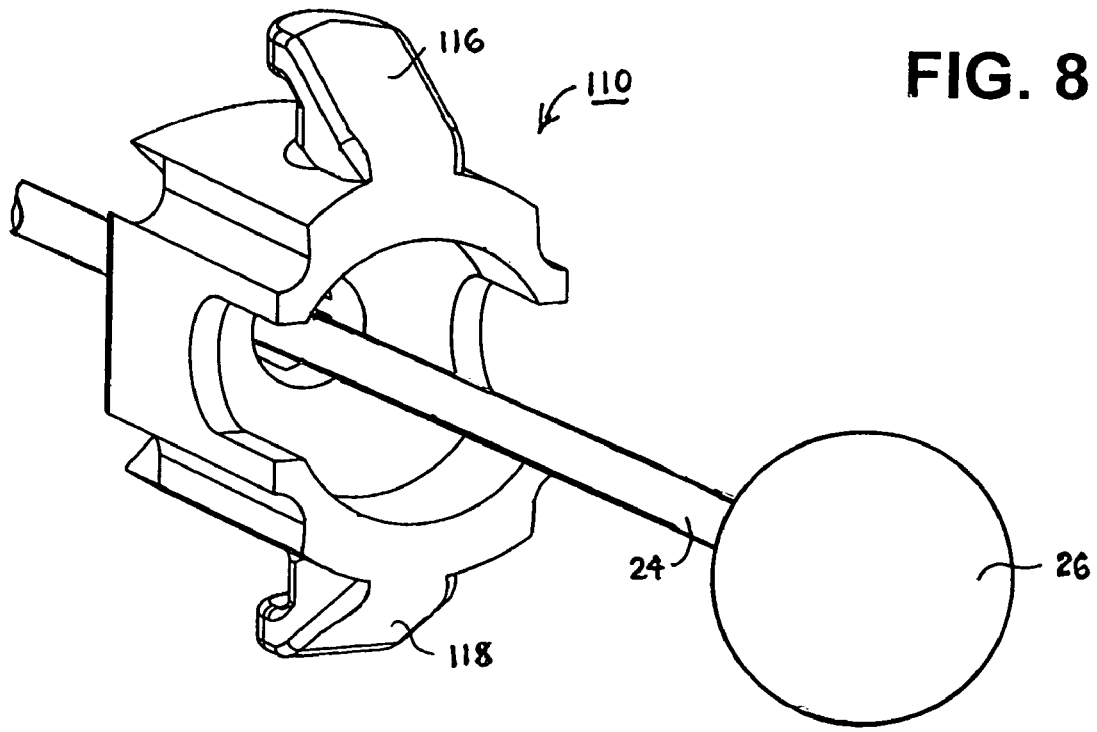
FIG. 8 is an exploded perspective view of the cable tab of FIG. 7 with a cable ball attached to the cable distal end.

The metal cable tab 110 shown in detail in FIGS. 7 and 8 is generally rectangular and extends between cable tab proximal end 112 and cable tab distal end 114. Opposed tabs 116 and 118 extend outward of the cylindrical sidewalls of the cable tab 110. The flattened sides of the cable tab 110 are sized to fit within the distal link recess 100 so that the opposed tabs 116 and 118 project outward and can be engaged in the tab openings 86 and 88, respectively, of the lower and upper sling arms 82 and 84, respectively.

A concave recess is formed in the cable tab distal end 114 that is shaped and dimensioned to receive the cable ball 26 as shown in FIG. 8. An oversize cable lumen 111 extends from the convex recess through the cable tab proximal end 112 that the tensioning cable 24 extends through. Four corner vacuum channels or grooves 113, 115, 117 and 119 are formed extending from the cable tab proximal end 112 to the cable tab distal end 114 that are axially aligned with the vacuum lumens 103, 105, 107, 109 through the head link distal end 94 when the cable tab 110 is fitted into the link cavity 100.

In assembly, the distal end of the tensioning cable 24 (not yet attached to the distal cable ball 26) is advanced through the head link cable lumen 101, out of the head link cavity 100 and through the cable tab lumen 111. The distal end of the tensioning cable 24 is attached to the cable ball 26, and the cable ball 26 and cable tab 110 are fitted into the head link cavity 100 with the tabs 116 and 118 projection outward. The concave head link distal end 94 is applied against the proximal articulating surfaces 66 and 68. The sling 80 is fitted over the split ball spreading mechanism 52 of the U-shaped, insert mold assembly 50 and moved proximally over the surfaces 102 and 104 of the head link cavity until the tabs 116 and 118 slip into the tab openings 86 and 88, respectively. The stabilizer pods 32 and 34 are fitted over the malleable tubes 72 and 74, respectively, and adhered to arms 62 and 64, respectively. The suction member sub-assembly 30' depicted in FIG. 2 is thereby assembled.

The outer sealing sleeve 40 is preferably formed of a transparent flexible plastic material, e.g., silicone rubber, which can be stretched up to 800%, for example, to fit over the other assembled components. The stretching enables the stabilizer pods 32 and 34 and the respective laterally extending arms 62 and 64 to be fitted through the openings surrounded by the sealing rings 46 and 48, respectively, to fit the sealing rings 46 and 48 into the circumferential grooves 56 and 58, respectively, and enables the outer sealing sleeve 40 to resume the shape depicted in FIG. 1. It would also be possible to insert the malleable tubes 72 and 74 and the respective laterally extending arms 62 and 64 to be fitted through the openings surrounded by the sealing rings 46 and 48, respectively, and to fit the sealing rings 46 and 48 into the circumferential grooves 56 and 58, respectively, before the stabilizer pods 32 and 34 are fitted over the respective malleable tubes 72 and 74. In either approach, a proximal segment of the outer sealing sleeve is adhered to the articulating arm outer sleeve 18.

In use, a vacuum can be drawn into the link cavity 100 from the vacuum source coupled to the vacuum port 124 through the clearance between the tensioning cable 24 and the head link cable lumen 101 defining the arm vacuum lumen and the vacuum channels or grooves 113, 115, 117 and 119 axially aligned with the respective vacuum lumens 103, 105, 107, 109. The vacuum is further drawn through the lumens of the malleable tubes 72 and 74, the split 54, and the head link distal lumen 98, whereby suction is applied to tissue contacting the suction ports 37 and 39.

Figure 10:
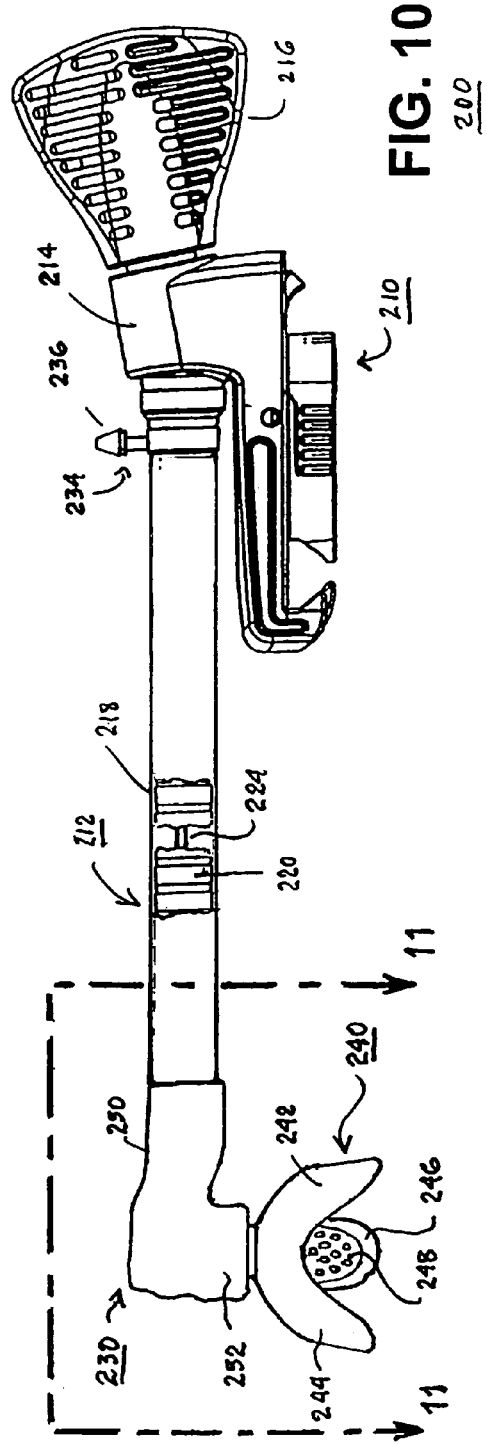
FIG. 10 is a side view of a second preferred embodiment of a suction-assisted, tissue-engaging device comprising an elongated articulating arm extending between a proximal knob and a distal suction member comprising a suction pad having three flexible appendages or legs.
Figure 11:
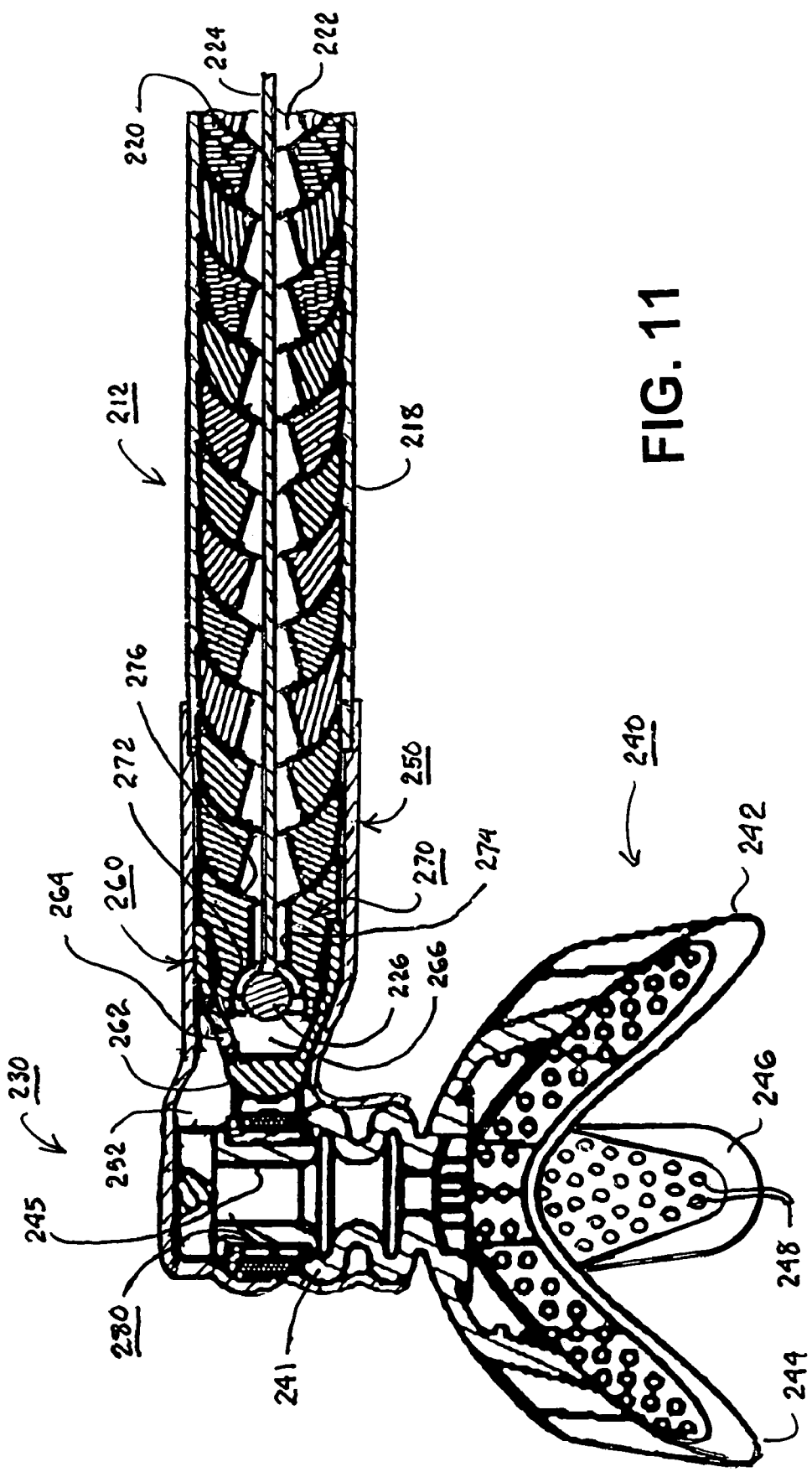
FIG. 11 is a side cross-section view taken along lines 11-11 of FIG. 10 depicting the distal suction member coupled to the articulating arm distal end entrapping the cable ball and the internal vacuum passageway from the articulating arm lumen to the plurality of suction ports.

A second embodiment of a suction-assisted tissue-engaging device 200 embodying features of the present invention is illustrated in FIGS. 10-12 wherein a suction member 230 is configured to engage body tissue and function in this embodiment as an organ positioner, particularly a heart positioner. The suction-assisted tissue-engaging device 200 comprises an elongated articulating arm 212 extending between a proximal clamp 210 and tensioning knob 216 and a distal suction member 230. The articulating arm 212 comprises an outer sheath 218 that extends from an outer sheath 250 of the distal suction member 230 to a clamp fitting 214 of the clamp 210. The exemplary clamp 210 at the proximal end of the articulating arm 212 depicted in FIG. 10 can be mounted to a sternal retractor 150, e.g., the Medtronic® OctoBase™ sternal retractor, as shown in FIG. 12. The components and operation of the clamp 210 may correspond to those described in the above-referenced, commonly assigned '769 patent, particularly with reference to FIG. 3 thereof.

The elongated articulating arm 212 comprises a plurality of articulating links 220 that are strung over a flexible tensioning cable 224 that extends between a distal cable ball 226 shown in FIG. 11 and a proximal connection with the tensioning knob 216. The articulating links 220, tensioning cable 224 and proximal tensioning knob 216 are configured and function in substantially the same way as the articulating links 120 tensioning cable 24 and proximal tensioning knob 16 as described above. The articulating links 220 and tensioning cable 224 are encased within the lumen of the flexible outer sheath 218 to prevent ingress of body fluids or tissue that might interfere with the articulation of the links 220. In accordance with the present invention, a vacuum is also drawn from vacuum port 234 through an arm vacuum lumen through the flexible outer sheath lumen between the cable 224 and the aligned link bores 222.

The suction head 230 comprises a suction pad 240, a head link 260, a cable tab 270, and a support ring 280, all covered at least in part by a flexible boot 250 having a proximal segment thereof that is adhered to a distal segment of the outer sheath 218. Generally speaking, the suction head 230 can be manually adjusted from the generally 90° relationship to the articulating arm axis depicted in FIGS. 11 and 12 independently of the manual manipulation of the articulating arm 212 into a preferred configuration and the rotation of the proximal tensioning knob 216 in the tightening or loosening direction. The proximal tensioning knob 216 is rotated in the tightening direction to both make the articulating arm rigid and to compress a distal seal in order to seal the arm vacuum lumen from leakage proximal to the vacuum port 234.

In this regard, the vacuum port 234 is formed as an integral part of an articulating link 220 corresponding to articulating link $120_n$ as described above or the clamp fitting 214. In either case, a resilient seal is fitted between the articulating link 220 and a more proximal articulating link or a non-articulating link or the clamp fitting 214. The resilient seal can comprise the conical seal 130 of FIG. 2 fitted into a conical link bore opening 222 or a resilient silicone rubber washer fitted into a seat or the like around the tensioning cable 226. In any case, the resilient seal is compressed into its seat or link bore 222 and against the tensioning cable 224 as the proximal tensioning knob 216 is rotated in the tightening direction to prevent any loss of vacuum drawn through the vacuum port 224 proximally to the vacuum port 224. The locked together, convex and concave, mating ends of the articulating links 220 and the flexible outer sheath 218 prevent any loss of vacuum along the length of the arm vacuum lumen within the articulating arm 212. In use, as shown in FIG. 12, a vacuum is drawn through suction ports 248 and the lumen of the articulating arm 212 by a vacuum source coupled to vacuum port fitting 236 of vacuum port 234 by a vacuum hose or line 142.

The suction pad 240 can take any of the shapes of and incorporate any of the features of the suction pads employed in the above-referenced Starfish™ heart positioner and/or as disclosed in the above-referenced, commonly assigned, Publication No. 2002/0095067 having a plurality of legs, e.g., two to four legs. The illustrated suction pad 240 has three legs 242, 244, 246 that diverge outward in a generally starfish-shaped configuration and downward from a bellows-shaped, tubular pad shaft 241 that is received within the ring shaped support ring 280. A suction pad lumen 245 extends through the pad shaft 241 and diverges into suction channels within the three legs 242, 244, 246.

The legs 242, 244, 246 preferably are generally arcuate, curving downwardly away the head shaft segment 252 to the free ends of the legs 242, 244, 246. Suction ports 248 extend from suction channels within the suction pad 240 through the inner wall of the legs 242, 244, 246. Preferably, the suction pad 240 and the legs 242, 244, 246 are formed integrally of substantially transparent or translucent medical grade silicone or thermoplastic elastomeric material (e.g., polyurethane). The material selected most preferably has a low durometer so that the suction pad 240 and the legs 242, 244, 246 tend to conform to the surface of the heart and to flex to help seal against the heart to maintain the vacuum in the internal vacuum channels. The suction pad 240 is preferably sufficiently flexible such that the suction pad 240 draws down toward the surface of the heart more than the surface of the heart is pulled into the suction ports 248.

A cable tab 270 is shaped similarly to the cable tab 110 having concave proximal end 276 that mates with a convex distal end of the most distal articulating link 220 and a concave, hemispheric distal end that mates with and receives the cable ball 226. The cable 224 extends through an enlarged diameter lumen 274 of the cable tab 270, and vacuum channels 272 are formed extending into the concave, hemispheric distal end that receives the cable ball 226. In this way, a head vacuum channel extends from the link bore 222 of the most distal articulating link 220 through the cable tab lumen 274 and the vacuum channels 272 to the head link bore 266 of head link 260.

The head link 260 extends between a concave head link proximal end and a convex head link distal end 262 and encloses a head link bore 266. A convex proximal end of the cable tab 270 fits into the concave proximal end of the head link 260, and the convex cable tab distal end 262 fits against the support ring 280. A vacuum port 264 extends through the head link 260 connecting the outer sheath lumen 252 with the head link bore 266. The outer sheath lumen 252 is open to the suction pad lumen 245 that extends through leg suction channels to the suction ports 248 of the legs 242, 244, 246. In this way, the head vacuum channel extends further from the head link bore 266 to the suction ports 248.

In use as shown in FIG. 12, the clamp 210 is attached to the sternal retractor 150, and the proximal tensioning knob 216 is rotated in the loosening direction to allow the articulating arm 212 to be manipulated. A vacuum line 142 extending to an operating room vacuum source that preferably provides a negative pressure of about 400 mm Hg is attached to the vacuum port fitting 226. A stopcock (not shown) can be provided in the vacuum line 142 to provide or interrupt suction as necessary during the procedure. Initially, the stopcock would be closed.

As described in the above-referenced, commonly assigned, Publication No. 2002/0095067, the physician can manually shape the articulating arm 212 and lift and move the heart to apply the suction pad 240 and legs 242, 244, 246 against the heart at a site that allows the heart to be engaged by the applied suction and held in a desired non-physiologic position. The shape of the legs 242, 244, 446 allow the suction pad 240 to be oriented to avoid placement over particular features of the heart anatomy, such as the cardiac arteries, or to avoid conflict with other devices employed in the medical procedure. When accessing various walls of the heart, the suction pad 240 can be preferably applied in one of two positions depending on the anatomy of the patient and the walls of the heart to be accessed. The first position is directly on the apex of the heart, which can be used for positioning for access to the lateral wall, posterior wall, or anterior wall of the heart. The second position is an off-apex position immediately adjacent to the apex. In particular, the suction pad 240 can be attached to the left ventricle immediately lateral to the apex of the heart. This particular off-apex position is especially useful for accessing the lateral wall in "apex under right hemisternum" position since even modest rightward movement of the apex greatly enhances exposure of proximal obtuse marginals. Thus, the suction pad 240 can be effectively applied to the heart not only on the apex but also to near-apex surfaces of the heart when that positioning would be desirable. The references herein to "near-apex", "near the apex of the heart" or the like includes application of the suction pad 240 onto the apex or onto other surfaces of the heart immediately adjacent to the apex.

Once the suction pad 240 and the heart are positioned, the proximal tensioning knob 216 is rotated in the tightening direction to seal the articulating arm vacuum lumen from leakage. The stopcock is opened to apply suction through the vacuum port 224, the articulating arm vacuum lumen, and the head lumen to cause the legs 242, 244, 246 to grasp the surface of the heart. The proximal tensioning knob 216 is rotated further in the tightening direction to make the articulating arm rigid.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

What is claimed is:

1. A suction-assisted tissue-engaging device adapted to be used in a method of performing a medical procedure on body tissue accessed through an incision into a body cavity, comprising:

an elongated articulating arm extending between an articulating arm proximal end and an articulating arm distal end enclosing an arm vacuum lumen coupled with a vacuum port for drawing a vacuum through the arm vacuum lumen, the articulating arm adapted to be manipulated in a flexible state into an operative shape and changed into a rigid state maintaining the operative shape, wherein the arm vacuum lumen exhibits a vacuum leak when the articulating arm is in the flexible state, and wherein the vacuum leak is sealed as the articulating arm is changed from the flexible state to the rigid state; and a suction member coupled to the articulating arm distal end having a suction member vacuum lumen coupled with the arm vacuum lumen extending to at least one suction port adapted to be applied against the body organ, whereby vacuum drawn through the vacuum port provides suction at the suction port to engage body tissue.

2. A suction-assisted tissue-engaging device adapted to be used in method of performing a medical procedure on body tissue accessed through an incision into a body cavity, comprising:

an elongated articulating arm extending between an articulating arm proximal end and an articulating arm distal end enclosing an arm vacuum lumen coupled with a vacuum port for drawing a vacuum through the arm vacuum lumen, the articulating arm adapted to be manipulated in a flexible state into an operative shape and changed into a rigid state maintaining the operative shape; and a suction member coupled to the articulating arm distal end having a suction member vacuum lumen coupled with the arm vacuum lumen extending to at least one suction port adapted to be applied against the body organ, whereby vacuum drawn through the vacuum port provides suction at the suction port to engage body tissue, wherein the arm vacuum lumen exhibits a vacuum leak when the articulating arm is in the flexible state; and sealing means for sealing the vacuum leak as the articulating arm is changed from the flexible state to the rigid state.

3. The tissue-engaging device of claim 2, further comprising:

tensioning means coupled to the elongated articulating arm adapted to be selectively operated to render the articulating arm in the flexible state enabling manipulation of the articulating arm into the operative shape, wherein the arm vacuum lumen exhibits a vacuum leak, and is selectively operated to render the articulating arm in the rigid state maintaining the operative shape imparted to the articulating arm; and wherein:

the sealing means seals the vacuum leak as the tensioning means is operated to change the flexible state to the rigid state.

4. The tissue-engaging device of claim 3, wherein the articulating arm further comprises:

an elongated flexible outer sheath having an outer sheath lumen extending between an outer sheath distal end coupled to the suction member and an outer sheath proximal end coupled to the articulating arm proximal end;

a plurality of interlocking articulating links within the outer sheath lumen, the articulating links each having a link proximal end and a link distal end and a link bore extending between the link proximal and distal ends, the link proximal and distal ends of adjacent articulating links shaped to provide end-to-end articulation with the link bores aligned; and an elongated tensioning cable extending through the articulating link bores between a cable proximal end and a cable distal end proximate the suction member, whereby the aligned link bores provide the arm vacuum lumen alongside the elongated tensioning cable.

5. The tissue-engaging device of claim 4, wherein the tensioning means is coupled to the cable proximal end and is selectively operable to release tension in the tensioning cable to render the articulating arm in a flexible state enabling manipulation of the articulating arm into an operative shape and to impart tension to the tensioning cable to draw the mating link proximal and distal ends together to render the articulating arm in a rigid state and maintain the articulating arm in the operative shape.

6. The tissue-engaging device of claim 5, wherein the sealing means further comprises a resilient seal having a seal bore and is fitted into a seal seat of an articulating link or non-articulating link distal to the tensioning means with the tensioning cable extending through the seal bore, and the seal is compressed against the tensioning cable and seal seat preventing any vacuum leak proximal to the seal seat when the articulating arm is in the rigid state.

7. The tissue-engaging device of claim 6, wherein the vacuum port extends from the link bore of an articulating link or a non-articulating link disposed distal to the seal seat that the resilient seal is fitted into.

8. The tissue-engaging device of claim 7, wherein the resilient seal and seal bore are dimensioned with respect to the seal seat and the tensioning cable such that the resilient seal is compressible against the seal seat and the tensioning cable sufficient to reduce vacuum leak proximal to the seal seat as the tensioning cable is drawn proximally while the articulating arm remains in the flexible state allowing manipulation of the articulating arm into an operative shape.

9. The tissue-engaging device of claim 6, wherein the resilient seal and seal bore are dimensioned with respect to the seal seat and the tensioning cable such that the resilient seal is compressible against the seal seat and the tensioning cable sufficient to reduce vacuum leak proximal to the seal seat as the tensioning cable is drawn proximally while the articulating arm remains in the flexible state allowing manipulation of the articulating arm into an operative shape.

10. The tissue-engaging device of claim 1, wherein the articulating arm further comprises:

an elongated flexible outer sheath having an outer sheath lumen extending between an outer sheath distal end coupled to the suction member and an outer sheath proximal end coupled to the articulating arm proximal end;

a plurality of interlocking articulating links within the outer sheath lumen, the articulating links each having a link proximal end and a link distal end and a link bore extending between the link proximal and distal ends, the link proximal and distal ends of adjacent articulating links shaped to provide end-to-end articulation with the link bores aligned; and an elongated tensioning cable extending through the articulating link bores between a cable proximal end and a cable distal end proximate the suction member, whereby the aligned link bores provide the arm vacuum lumen alongside the elongated tensioning cable.

11. The tissue-engaging device of claim 10, further comprising tensioning means coupled to the cable proximal end that is selectively operable to release tension in the tensioning cable to render the articulating arm in a flexible state enabling manipulation of the articulating arm into an operative shape and to impart tension to the tensioning cable to draw the mating link proximal and distal ends together to render the articulating arm in a rigid state and maintain the articulating arm in the operative shape.

12. The tissue-engaging device of claim 11, wherein the distal suction member further comprises:

first and second distally extending stabilizer pods each having at least one suction port adapted to be applied against body tissue and coupled to the suction member vacuum lumen; and spreading means operable when suction is applied through the suction ports to the body tissue and responsive to tension imparted to the tensioning cable to render the articulating arm in the rigid state for spreading the stabilizer pods apart to stretch the body tissue between the first and second suction pods.

13. The suction-assisted tissue-engaging device of claim 11, wherein the distal suction member further comprises:
   a suction member sub-assembly coupled to the cable distal end incorporating the suction member vacuum lumen coupled with the arm vacuum lumen and supporting first and second suction pods to extend distally substantially in parallel and spaced apart from one another each having at least one suction port coupled to the suction member vacuum lumen adapted to be applied against body tissue to stabilize body tissue between the first and second suction pods when suction is applied to the body tissue to facilitate performing a medical procedure; and
   a suction member outer sealing sleeve extending over at least a portion of the suction member sub-assembly sealing the suction member vacuum lumen from vacuum leakage.

14. The tissue-engaging device of claim 13, wherein the suction member sub-assembly further comprises spreading means operable when suction is applied through the suction ports to the body tissue and responsive to tension imparted to the tensioning cable to render the articulating arm in the rigid state for spreading the stabilizer pods apart to stretch the body tissue between the first and second suction pods.

15. The tissue-engaging device of claim 1, further comprising:
   tensioning means coupled to the elongated articulating arm adapted to be selectively operated to render the articulating arm in the flexible state enabling manipulation of the articulating arm into the operative shape and selectively operated to render the articulating arm in the rigid state maintaining the operative shape imparted to the articulating arm; and
   wherein the distal suction member further comprises:
      first and second distally extending stabilizer pods each having at least one suction port coupled to the suction member vacuum lumen adapted to be applied against body tissue; and
      spreading means operable when suction is applied through the suction ports to the body tissue and responsive to tension imparted to the tensioning cable to render the articulating arm in the rigid state for spreading the stabilizer pods apart to stretch the body tissue between the first and second suction pods.

16. The suction-assisted tissue-engaging device of claim 1, wherein the distal suction member further comprises
   a suction member sub-assembly coupled to the cable distal end incorporating the suction member vacuum lumen coupled with the arm vacuum lumen and supporting first and second suction pods to extend distally substantially in parallel and spaced apart from one another each having at least one suction port coupled to the suction member vacuum lumen adapted to be applied against body tissue to stabilize body tissue between the first and second suction pods when suction is applied to the body tissue to facilitate performing a medical procedure; and
   a suction member outer sealing sleeve extending over at least a portion of the suction member sub-assembly sealing the suction member vacuum lumen from vacuum leakage.

17. The tissue-engaging device of claim 16, wherein the suction member sub-assembly further comprises means for spreading the stabilizer pods apart when the tensioning means is operated to render the articulating arm in the rigid state to stretch the body tissue between the first and second suction pods.

18. The tissue-engaging device of claim 1, wherein the suction member further comprises a suction pad diverging into a plurality of flexible appendages each having at least one suction port coupled to the suction member vacuum lumen and adapted to be applied against body tissue, the suction pad and appendages shaped to conform anatomically to an area of a body organ to enable the body organ to be moved into and maintained in a non-physiologic position within the body cavity to facilitate performing a medical procedure upon the body organ.

19. The tissue-engaging device of claim 18, wherein the articulating arm further comprises:
   an elongated flexible outer sheath having an outer sheath lumen extending between an outer sheath distal end coupled to the suction member and an outer sheath proximal end coupled to the articulating arm proximal end;
   a plurality of interlocking articulating links within the outer sheath lumen, the articulating links each having mating link proximal and distal ends and a link bore extending between the link proximal and distal ends; and
   an elongated tensioning cable extending through the articulating link bores between a cable proximal end and a cable distal end coupled to the suction member, whereby the aligned link bores provide the arm vacuum lumen alongside the elongated tensioning cable.

20. The tissue-engaging device of claim 19, further comprising tensioning means coupled to the cable proximal end that is selectively operable to release tension in the tensioning cable to render the articulating arm in a flexible state enabling manipulation of the articulating arm into an operative shape and to impart tension to the tensioning cable to draw the mating link proximal and distal ends together to render the articulating arm in a rigid state and maintain the articulating arm in the operative shape.

21. A method of applying suction to body tissue accessed through an incision into a body cavity for facilitating a medical procedure comprising:
   providing a suction-assisted, tissue-engaging device comprising:
      an elongated articulating arm extending between an articulating arm proximal end and an articulating arm distal end enclosing an arm vacuum lumen coupled with a vacuum port for drawing a vacuum through the arm vacuum lumen, the articulating arm adapted to be manipulated in a flexible state into an operative shape and changed into a rigid state maintaining the operative shape, wherein the arm vacuum lumen exhibits a vacuum leak when the articulating arm is in the flexible state; and
      a suction member coupled to the articulating arm distal end having a suction member lumen coupled with the arm vacuum lumen extending to at least one suction port adapted to be applied against the body organ, whereby vacuum drawn through the vacuum port, the arm vacuum lumen and the suction port engages body tissue;
   fixing the articulating arm proximal end to a fixed position in relation to the body tissue;
   shaping the articulating arm into an operative shape disposing the suction port against the body tissue while the articulating arm is in the flexible state;

coupling the vacuum port to a vacuum source;
drawing a vacuum through the arm vacuum lumen and the suction member vacuum lumen to apply suction through the suction port to body tissue to grasp the body tissue; and
changing the articulating arm into the rigid state maintaining the operative shape, wherein the vacuum leak is sealed as the articulating arm is changed from the flexible state to the rigid state.

22. The method of claim 21, wherein the distal suction member further comprises first and second distally extending stabilizer pods each having at least one suction port adapted to be applied against body tissue and coupled to the suction member vacuum lumen, and further comprising:
spreading the stabilizer pods apart to stretch the body tissue between the first and second suction pods when suction is applied through the suction ports to the body tissue.

23. A method of applying suction to body tissue accessed through an incision into a body cavity for facilitating a medical procedure comprising:
providing a suction-assisted, tissue-engaging device comprising:
an elongated articulating arm extending between an articulating arm proximal end and an articulating arm distal end enclosing an arm vacuum lumen coupled with a vacuum port for drawing a vacuum through the arm vacuum lumen, the articulating arm adapted to be manipulated in a flexible state into an operative shape and changed into a rigid state maintaining the operative shape; and
a suction member coupled to the articulating arm distal end having a suction member lumen coupled with the arm vacuum lumen extending to at least one suction port adapted to be applied against the body organ, whereby vacuum drawn through the vacuum port, the arm vacuum lumen and the suction port engages body tissue, wherein the suction member further comprises first and second distally extending stabilizer pods each having at least one suction port adapted to be applied against body tissue and coupled to the suction member vacuum lumen;
fixing the articulating arm proximal end to a fixed position in relation to the body tissue;
shaping the articulating arm into an operative shape disposing the suction port against the body tissue while the articulating arm is in the flexible state;
coupling the vacuum port to a vacuum source;
drawing a vacuum through the arm vacuum lumen and the suction member vacuum lumen to apply suction through the suction port to body tissue to grasp the body tissue;
changing the articulating arm into the rigid state maintaining the operative shape;
spreading the stabilizer pods apart to stretch the body tissue between the first and second suction pods when suction is applied through the suction ports to the body tissue, wherein the arm vacuum lumen exhibits a vacuum leak when the articulating arm is in the flexible state; and
sealing the vacuum leak as the articulating arm is changed from the flexible state to the rigid state.

24. A method of applying suction to body tissue accessed through an incision into a body cavity for facilitating a medical procedure comprising:
providing a suction-assisted, tissue-engaging device comprising:
an elongated articulating arm extending between an articulating arm proximal end and an articulating arm distal end enclosing an arm vacuum lumen coupled with a vacuum port for drawing a vacuum through the arm vacuum lumen, the articulating arm adapted to be manipulated in a flexible state into an operative shape and changed into a rigid state maintaining the operative shape; and
a suction member coupled to the articulating arm distal end having a suction member lumen coupled with the arm vacuum lumen extending to at least one suction port adapted to be applied against the body organ, whereby vacuum drawn through the vacuum port, the arm vacuum lumen and the suction port engages body tissue;
fixing the articulating arm proximal end to a fixed position in relation to the body tissue;
shaping the articulating arm into an operative shape disposing the suction port against the body tissue while the articulating arm is in the flexible state;
coupling the vacuum port to a vacuum source;
drawing a vacuum through the arm vacuum lumen and the suction member vacuum lumen to apply suction through the suction port to body tissue to grasp the body tissue;
changing the articulating arm into the rigid state maintaining the operative shape, wherein the arm vacuum lumen exhibits a vacuum leak when the articulating arm is in the flexible state; and
sealing the vacuum leak as the articulating arm is changed from the flexible state to the rigid state.

25. The method of claim 21, wherein:
the articulating arm further comprises:
an elongated flexible outer sheath having an outer sheath lumen extending between an outer sheath distal end coupled to the suction member and an outer sheath proximal end coupled to the articulating arm proximal end;
a plurality of interlocking articulating links within the outer sheath lumen, the articulating links each having a link proximal end and a link distal end and a link bore extending between the link proximal and distal ends, the link proximal and distal ends of adjacent articulating links shaped to provide end-to-end articulation with the link bores aligned; and
an elongated tensioning cable extending through the articulating link bores between a cable proximal end and a cable distal end proximate the suction member, whereby the aligned link bores provide the arm vacuum lumen alongside the elongated tensioning cable; and
the changing step further comprises retracting the tensioning cable proximally to draw the link proximal and distal ends of adjacent articulating links into end-to-end contact that frictionally resists movement and maintains the articulating arm in the operative shape.

26. A method of applying suction to body tissue accessed through an incision into a body cavity for facilitating a medical procedure comprising:
providing a suction-assisted, tissue-engaging device comprising:
an elongated articulating arm extending between an articulating arm proximal end and an articulating arm distal end enclosing an arm vacuum lumen coupled with a vacuum port for drawing a vacuum through the arm vacuum lumen, the articulating arm adapted to be manipulated in a flexible state into an operative shape and changed into a rigid state maintaining the operative shape; and
a suction member coupled to the articulating arm distal end having a suction member lumen coupled with the arm vacuum lumen extending to at least one suction port adapted to be applied against the body organ, whereby vacuum drawn through the vacuum port, the arm vacuum lumen and the suction port engages body tissue;

fixing the articulating arm proximal end to a fixed position in relation to the body tissue;

shaping the articulating arm into an operative shape disposing the suction port against the body tissue while the articulating arm is in the flexible state;

coupling the vacuum port to a vacuum source;

drawing a vacuum through the arm vacuum lumen and the suction member vacuum lumen to apply suction through the suction port to body tissue to grasp the body tissue; and changing the articulating arm into the rigid state maintaining the operative shape, wherein the articulating arm further comprises:

an elongated flexible outer sheath having an outer sheath lumen extending between an outer sheath distal end coupled to the suction member and an outer sheath proximal end coupled to the articulating arm proximal end;

a plurality of interlocking articulating links within the outer sheath lumen, the articulating links each having a link proximal end and a link distal end and a link bore extending between the link proximal and distal ends, the link proximal and distal ends of adjacent articulating links shaped to provide end-to-end articulation with the link bores aligned; and an elongated tensioning cable extending through the articulating link bores between a cable proximal end and a cable distal end proximate the suction member, whereby the aligned link bores provide the arm vacuum lumen alongside the elongated tensioning cable; and the changing step further comprises retracting the tensioning cable proximally to draw the link proximal and distal ends of adjacent articulating links into end-to-end contact that frictionally resists movement and maintains the articulating arm in the operative shape, wherein the arm vacuum lumen exhibits a vacuum leak when the articulating arm is in the flexible state; and sealing the vacuum leak as the articulating arm is changed from the flexible state to the rigid state.

27. The method of claim 26, wherein:

the articulating arm further comprises a resilient seal having a seal bore and fitted into a seal seat of an articulating link or non-articulating link distal to the cable proximal end with the tensioning cable extending through the seal bore;

and the sealing step comprises compressing the resilient seal against the tensioning cable and seal seat preventing any vacuum leak proximal to the seal seat during the changing step.

28. The method of claim 27, wherein the vacuum port extends from the link bore of an articulating link or a non-articulating link disposed distal to the seal seat that the resilient seal is fitted into.

29. The method of claim 28, wherein the resilient seal and seal bore are dimensioned with respect to the seal seat and the tensioning cable such that the resilient seal is compressible against the seal seat and the tensioning cable sufficient to reduce vacuum leak proximal to the seal seat as the tensioning cable is drawn proximally while the articulating arm remains in the flexible state allowing manipulation of the articulating arm into an operative shape.

30. The method of claim 21, wherein the suction member further comprises a suction pad diverging into a plurality of flexible appendages each having at least one suction port coupled to the suction member vacuum lumen and adapted to be applied against body tissue, the suction pad and appendages shaped to conform anatomically to an area of a body organ to enable the body organ to be moved into and maintained in a non-physiologic position within the body cavity to facilitate performing a medical procedure upon the body organ.

31. A method of applying suction to body tissue accessed through an incision into a body cavity for facilitating a medical procedure comprising:

providing a suction-assisted, tissue-engaging device comprising:

an elongated articulating arm extending between an articulating arm proximal end and an articulating arm distal end enclosing an arm vacuum lumen coupled with a vacuum port for drawing a vacuum through the arm vacuum lumen, the articulating arm adapted to be manipulated in a flexible state into an operative shape and changed into a rigid state maintaining the operative shape, the elongated articulating arm exhibiting a vacuum leak from the arm vacuum lumen when in the flexible state; and a suction member coupled to the articulating arm distal end having a suction member lumen coupled with the arm vacuum lumen extending to at least one suction port adapted to be applied against the body organ, whereby vacuum drawn through the vacuum port, the arm vacuum lumen and the suction port engages body tissue;

fixing the articulating arm proximal end to a fixed position in relation to the body tissue;

sealing the vacuum leak by changing the articulating arm from the flexible state into a sealed state;

coupling the vacuum port to a vacuum source;

drawing a vacuum through the arm vacuum lumen and the suction member vacuum lumen to apply suction through the suction port to body tissue to grasp the body tissue;

shaping the articulating arm into an operative shape disposing the suction port against the body tissue while the articulating arm is in the flexible state; and changing the articulating arm into the rigid state maintaining the operative shape.

32. The method of claim 31, wherein:

the articulating arm further comprises:

an elongated flexible outer sheath having an outer sheath lumen extending between an outer sheath distal end coupled to the suction member and an outer sheath proximal end coupled to the articulating arm proximal end;

a plurality of interlocking articulating links within the outer sheath lumen, the articulating links each having a link proximal end and a link distal end and a link bore extending between the link proximal and distal ends, the link proximal and distal ends of adjacent articulating links shaped to provide end-to-end articulation with the link bores aligned;

an elongated tensioning cable extending through the articulating link bores between a cable proximal end and a cable distal end proximate the suction member, whereby the aligned link bores provide the arm vacuum lumen alongside the elongated tensioning cable; and a resilient seal having a seal bore and fitted into a seal seat of an articulating link or non-articulating link distal to the cable proximal end with the tensioning cable extending through the seal bore;

the sealing step comprises compressing the resilient seal against the tensioning cable and seal seat preventing any vacuum leak proximal to the seal seat.

33. The method of claim 32, wherein:

the sealing step comprises retracting the tensioning cable proximally sufficiently to compress the resilient seal against the tensioning cable and seal seat preventing any vacuum leak proximal to the seal seat; and the changing step further comprises further retracting the tensioning cable proximally to draw the link proximal and distal ends of adjacent articulating links into end-to-end contact that frictionally resists movement and maintains the articulating arm in the operative shape.

34. The method of claim 33, wherein the vacuum port extends from the link bore of an articulating link or a non-articulating link disposed distal to the seal seat that the resilient seal is fitted into.

35. The method of claim 31, wherein the distal suction member further comprises first and second distally extending stabilizer pods each having at least one suction port adapted to be applied against body tissue and coupled to the suction member vacuum lumen, and further comprising:

spreading the stabilizer pods apart to stretch the body tissue between the first and second suction pods when suction is applied through the suction ports to the body tissue.

36. The method of claim 31, wherein the suction member further comprises a suction pad diverging into a plurality of flexible appendages each having at least one suction port coupled to the suction member vacuum lumen and adapted to be applied against body tissue, the suction pad and appendages shaped to conform anatomically to an area of a body organ to enable the body organ to be moved into and maintained in a non-physiologic position within the body cavity to facilitate performing a medical procedure upon the body organ.

* * * * *